US006495547B1

(12) United States Patent
Wigerinck et al.

(10) Patent No.: US 6,495,547 B1
(45) Date of Patent: *Dec. 17, 2002

(54) (BENZODIOXAN, BENZOFURAN OR BENZOPYRAN) DERIVATIVES HAVING FUNDIC RELAXATION PROPERTIES

(75) Inventors: Piet Tom Bert Paul Wigerinck, Vosselaar; Wim Gaston Verschueren, Berchem; Marc Francis Josephine Schroven, Wiekevorst; Marcel Frans Leopold De Bruyn, Wortel, all of (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/641,485

(22) Filed: Aug. 18, 2000

Related U.S. Application Data

(62) Division of application No. 09/192,686, filed on Nov. 16, 1998, now Pat. No. 6,133,277.

(30) Foreign Application Priority Data

Dec. 5, 1997 (EP) .............................. 97203808

(51) Int. Cl.[7] ..................... C07D 405/14; C07D 405/12; C07D 417/14; C07D 417/12; A61K 31/517

(52) U.S. Cl. .................... 514/222.8; 514/259; 514/269; 514/274; 544/8; 544/11; 544/285; 544/316; 544/287; 544/324; 544/332; 544/355; 544/333; 544/364; 544/376; 544/377

(58) Field of Search ............................... 544/8, 11, 285, 544/316, 287, 324, 332, 355, 333, 364, 376, 377; 514/274, 222.8, 259, 269

(56) References Cited

U.S. PATENT DOCUMENTS

| 3,910,930 A | * 10/1975 | Janssen et al. ......... 260/293.58 |
| 4,239,348 A | * 12/1980 | Huebner et al. ............ 424/251 |
| 5,137,901 A | * 8/1992 | Junge et al. ................ 514/373 |
| 5,371,094 A | * 12/1994 | Heine et al. ................ 514/323 |
| 5,492,918 A | * 2/1996 | Wild et al. .................. 514/322 |

(List continued on next page.)

FOREIGN PATENT DOCUMENTS

| EP | 0 628 310 A1 | * 5/1994 |
| EP | 0 546 388 B1 | * 3/1996 |
| WO | WO 93/17017 | * 9/1993 |
| WO | WO 95/05383 | * 2/1995 |
| WO | WO 97/28157 | * 8/1997 |

Primary Examiner—Mark L. Berch
Assistant Examiner—Kahsay Habte

(57) ABSTRACT

The present invention of compounds of formula (I)

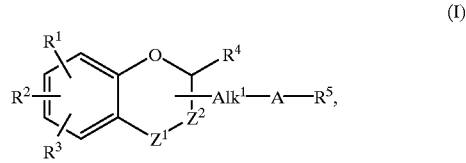

(I)

a stereochemically isomeric form thereof, an N-oxide form thereof or a pharmaceutically acceptable acid addition salt thereof, wherein $Alk^1$ is $C_{1-6}$alkanediyl optionally substituted with hydroxy, $C_{1-4}$alkyloxy or $C_{1-4}$alkylcarbonyloxy; $—Z^1—Z^2—$ is a bivalent radical; $R^1$, $R^2$ and $R^3$ are each independently selected from hydrogen, $C_{1-6}$alkyl, hydroxy, halo and the like; or when $R^1$ and $R^2$ are on adjacent carbon atoms, $R_1$ and $R^2$ taken together may form a bivalent radical; $R^4$ is hydrogen or $C_{1-6}$alkyl; A is a bivalent radical of formula $—NR^6—Alk^2—$ (b-1), or $—Npiperidinyl-(CH_2)_m$ (b-2) wherein m is 0 or 1; $R^5$ is a radical of formula (c-1)

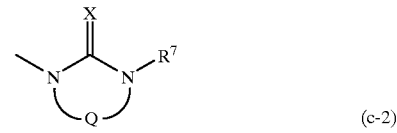

(c-2)

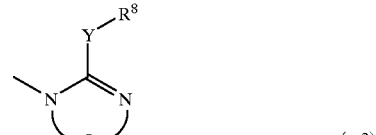

(c-3)

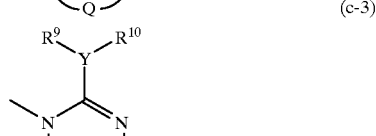

(c-4)

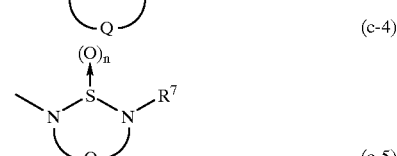

(c-5)

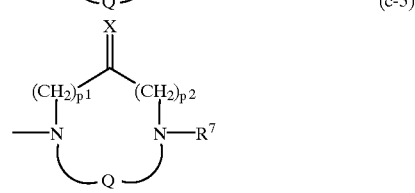

wherein n is 1 or 2; $p^1$ is 0, and $p_2$ is 1 or 2; or $p^1$ is 1 or 2, and $p^2$ is 0; X is oxygen, sulfur or $=NR^9$; Y is oxygen or sulfur; $R^7$ is hydrogen, $C_{1-6}$alkyl, $C_{3-6}$cycloalkyl, phenyl or phenylmethyl; $R^8$ is $C_{1-6}$alkyl, $C_{3-6}$cycloalkyl phenyl or phenylmethyl; $R^9$ is cyano, $C_{1-6}$alkyl, $C_{3-6}$cyclo-alkyl, $C_{1-6}$alkyloxycarbonyl or aminocarbonyl; $R^{10}$ is hydrogen or $C_{1-6}$alkyl; and Q is a bivalent radical. Processes for preparing said products, formulations comprising said products and their use as a medicine are disclosed, in particular for treating conditions which are related to impaired fundic relaxation.

12 Claims, No Drawings

U.S. PATENT DOCUMENTS 5,541,199 A * 7/1996 Memshaw et al. ........... 514/314
5,545,643 A * 8/1996 Heine et al. ................. 514/322
5,696,136 A * 12/1997 Heine et al. ................. 514/322
5,696,137 A * 12/1997 Heine et al. ................. 514/322
5,696,653 A * 12/1997 Heine et al. ................. 514/322
6,133,277 A * 10/2000 Wigernck et al. ........... 514/274

* cited by examiner

(BENZODIOXAN, BENZOFURAN OR BENZOPYRAN) DERIVATIVES HAVING FUNDIC RELAXATION PROPERTIES

CROSS REFERENCE TO RELATED APPLICATIONS

This application is a divisional application of U.S. Ser. No. 09/192,686 filed Nov. 16, 1998, now U.S. Pat. No. 6,133,277.

The present invention is concerned with novel aminomethylchromane compounds having fundic relaxation properties. The invention further relates to methods for preparing such compounds, pharmaceutical compositions comprising said compounds as well as the use as a medicine of said compounds.

Structurally related aminomethylchromane derivatives are disclosed in U.S. Pat. No. 5,541,199 as selective autoreceptor agonists useful as antipsychotic agents. Other structurally related aminomethylchroman derivatives having affinity for cerebral 5-hydroxytryptamine receptors of the 5-HT$_1$ type and therefore suitable for the treatment of disorders of the central nervous system are disclosed in U.S. Pat. No. 5,137,901.

EP-0,546,388, published on Jun. 16, 1993, discloses structurally related aminomethylchroman derivatives having affinity for cerebral 5-hydroxytryptamine receptors of the 5-HT$_1$ type and for dopamine receptors of the D$_2$-type. EP-0,628,310, published on Dec. 14, 1994, encompasses the use of the same aminomethylchroman derivatives for the inhibition of HIV-protease.

DE-2,400,094, published on Jul. 18, 1974, discloses 1-[1-[2-(1,4-benzodioxan-2-yl)-2-hydroxyethyl]-4-piperidyl-2-benzimidazolinones possessing blood pressure lowering activity.

WO-93/17017, published on Sep. 2, 1993, discloses [(benzodioxane, benzofuran or benzopyran)alkylamino]alkyl-substituted guanidine as selective vasoconstrictors useful to treat conditions related to vasodilatation such as, e.g., migraine, cluster headache and headache associated with vascular disorders.

WO-95/05383, published on Feb. 23, 1995, encompasses dihydrobenzopyranpyrimidine derivatives also having vasoconstrictive activity.

Other structurally related aminomethylchroman derivatives are disclosed in WO-97/28157, published on Aug. 7, 1997, as α$_2$-adrenergic receptor antagonists useful in the treatment of degenerative neurological conditions.

During the consumption of a meal the fundus, i.e. the proximal part of the stomach, relaxes and provides a "reservoir" function. Patients having an impaired adaptive relaxation of the fundus upon food ingestion have been shown to be hypersensitive to gastric distension and display dyspeptic symptoms. Therefore, it is believed that compounds which are able to normalize an impaired fundic relaxation are useful to relieve patients suffering from said dyspeptic symptoms.

The present invention concerns compounds of formula (I)

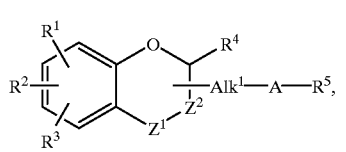

(I)

a stereochemically isomeric form thereof, an N-oxide form thereof or a pharmaceutically acceptable acid addition salt thereof, wherein Alk$^1$ is C$_{1-4}$alkylcarbonyl, C$_{1-4}$alkylcarbonylC$_{1-4}$alkyl, carbonyl, carbonylC$_{1-4}$alkyl, or C$_{1-6}$alkanediyl optionally substituted with hydroxy, C$_{1-4}$alkyloxy, C$_{1-4}$alkylcarbonyloxy, C$_{1-4}$alkylcarbonyloxyC$_{1-4}$alkyloxycarbonyloxy, or C$_{3-6}$cycloalkylcarbonyloxyC$_{1-4}$alkyloxycarbonyloxy;

—Z$^1$—Z$^2$— is a bivalent radical of formula

| —CH$_2$— | (e-1), | —CH= | (e-6), |
|---|---|---|---|
| —O—CH$_2$— | (e-2), | —CH$_2$—CH= | (e-7), |
| —S—CH$_2$— | (e-3), | —CH$_2$—CH$_2$—CH= | (e-8), |
| —CH$_2$—CH$_2$— | (e-4), | —CH=CH— | (e-9); |
| —CH$_2$—CH$_2$—CH$_2$— | (e-5), | | |

R$^1$, R$^2$ and R$^3$ are each independently selected from hydrogen, C$_{1-6}$alkyl, C$_{3-6}$alkenyl, C$_{1-6}$alkyloxy, trihalomethyl, trihalomethoxy, halo, hydroxy, cyano, nitro, amino. C$_{1-6}$alkylcarbonylamino, C$_{1-6}$alkyloxycarbonyl, C$_{1-4}$alkylcarbonyloxy, aminocarbonyl, mono- or di(C$_{1-6}$alkyl)aminocarbonyl, aminoC$_{1-6}$alkyl, mono- or di(C$_{1-6}$alkyl)aminoC$_{1-6}$alkyl, C$_{1-4}$alkylcarbonyloxyC$_{1-4}$alkyloxycarbonyloxy, or C$_{3-6}$cycloalkylcarbonyloxyC$_{1-4}$alkyloxycarbonyloxy, or when R$^1$ and R$^2$ are on adjacent carbon atoms, R$^1$ and R$^2$ taken together may form a bivalent radical of formula

| —CH$_2$—CH$_2$—Ch$_2$— | (a-1), | —O—CH$_2$—CH$_2$— | (a-6), |
|---|---|---|---|
| —CH$_2$—CH$_2$—CH$_2$—CH$_2$— | (a-2), | —O—CH$_2$—CH$_2$—O— | (a-7), |
| —CH$_2$—CH$_2$—CH$_2$—CH$_2$—CH$_2$— | (a-3), | —O—CH$_2$—CH$_2$—CH$_2$— | (a-8), |
| —CH=CH—CH=CH— | (a-4), | —O—CH$_2$—CH$_2$—CH$_2$—CH$_2$— | (a-9), |
| —O—CH$_2$—O— | (a-5), | | |

The compounds of the present invention differ from the cited art-known compounds structurally, by the nature of the R$^5$ substitutent, and pharmacologically by the fact that, unexpectedly, these compounds have fundic relaxation properties. Furthermore, the compounds of the present invention have additional beneficial pharmacological properties in that they have little or no vasoconstrictor activity.

wherein optionally one or two hydrogen atoms on the same or a different carbon atom may be replaced by hydroxy, C$_{1-4}$alkyl or CH$_2$OH;

R$^4$ is hydrogen, C$_{1-6}$alkyl, or a direct bond when the bivalent radical —Z$^1$—Z$^2$— is of formula (e-6). (e-7) or (e-8);

A is a bivalent radical of formula

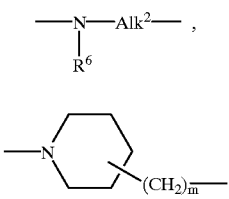

(b-1)

(b-2)

wherein the nitrogen atom is connected to $Alk^1$ and, m is 0 or 1;
$Alk^2$ is $C_{1-6}$alkanediyl;
$R^6$ is hydrogen, $C_{1-6}$alkyl, $C_{1-4}$alkylcarbonyl, $C_{1-4}$alkyloxycarbonyl, phenylmethyl, $C_{1-4}$alkylaminocarbonyl, $C_{1-4}$alkylcarbonyloxy$C_{1-4}$alkyloxycarbonyl, or $C_{3-6}$cycloalkylcarbonyloxy$C_{1-4}$alkyloxycarbonyloxy;
$R^5$ is a radical of formula

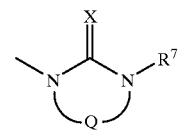 (c-1)

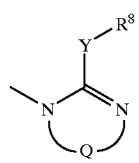 (c-2)

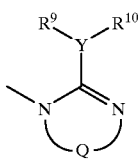 (c-3)

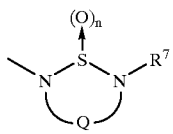 (c-4)

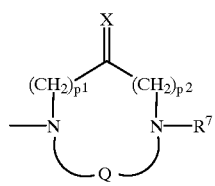 (c-5)

wherein n is 1 or 2;
$p^1$ is 0, and $p^2$ is 1 or 2; or
$p^1$ is 1 or 2, and $p^2$ is 0;
X is oxygen, sulfur, $NR^9$ or $CHNO_2$;
Y is oxygen or sulfur;
$R^7$ is hydrogen, $C_{1-6}$alkyl, $C_{3-6}$cycloalkyl, phenyl or phenylmethyl;
$R^8$ is $C_{1-6}$alkyl, $C_{3-6}$cycloalkyl, phenyl or phenylmethyl;

$R^9$ is cyano, $C_{1-6}$alkyl, $C_{3-6}$cycloalkyl, $C_{1-6}$alkyloxycarbonyl or aminocarbonyl;
$R^{10}$ is hydrogen or $C_{1-6}$alkyl; and
Q is a bivalent radical of formula

| | | | |
|---|---|---|---|
| —$CH_2$—$CH_2$— | (d-1), | —CH=CH— | (d-4), |
| —$CH_2$—$CH_2$—$CH_2$— | (d-2), | —$CH_2$—CO— | (d-5), |
| —$CH_2$—$CH_2$—$CH_2$—$CH_2$— | (d-3), | —CO—$CH_2$— | (d-6), | wherein optionally one or two hydrogen atoms on the same or a different carbon atom may be replaced by $C_{1-4}$alkyl, hydroxy or phenyl, or
Q is a bivalent radical of formula

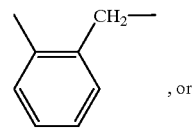 (d-7)

, or

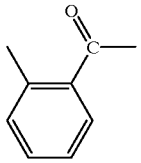 (d-8)

As used in the foregoing definitions halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like, $C_{1-6}$alkyl is meant to include $C_{1-4}$alkyl and the higher homologues thereof having 5 or 6 carbon atoms, such as, for example, 2-methyl-butyl, pentyl, hexyl and the like; $C_{3-6}$cycloalkyl is generic to cyclopropyl, cyclobutyl, cyclopentyl and cyclohexyl; $C_{1-3}$alkenyl defines straight and branched chain unsaturated hydrocarbon radicals having from 3 to 6 carbon atoms, such as propenyl, butenyl, pentenyl or hexenyl; $C_{1-2}$alkanediyl defines methylene or 1,2-ethanediyl; $C_{2-4}$alkanediyl defines bivalent straight or branched chain hydrocarbon radicals containing from 2 to 4 carbon atoms such as, for example, 1,2-ethanediyl, 1,3-propanediyl, 1,4-butanediyl, and the branched isomers thereof; $C_{1-5}$alkanediyl defines bivalent straight or branched chain hydrocarbon radicals containing from 1 to 5 carbon atoms such as, for example, methylene, 1,2-ethanediyl, 1,3-propanediyl, 1,4-butanediyl, 1,5-pentanediyl, and the branched isomers thereof; $C_{1-6}$alkanediyl includes $C_{1-5}$alkanediyl and the higher homologues thereof having 6 carbon atoms such as, for example, 1,6-hexanediyl and the like. The term "CO" refers to a carbonyl group.

Some examples of the $R^5$ moiety are

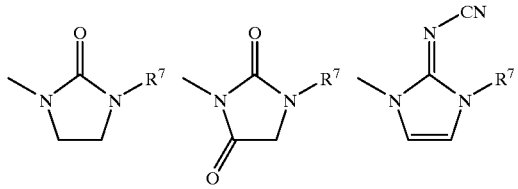

-continued

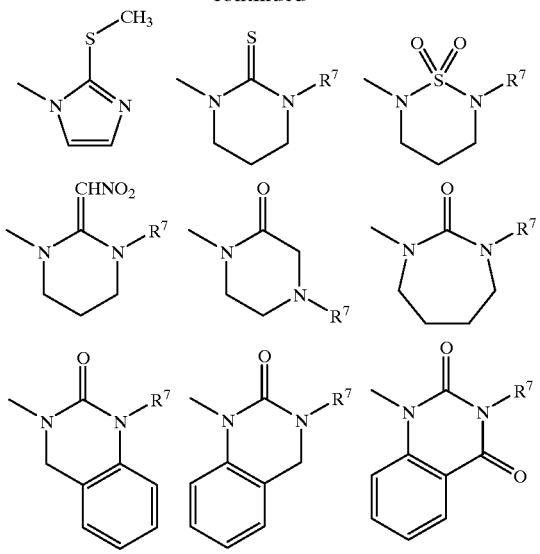

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I), which may be prepared in art-known manners, are meant to comprise those compounds of formula (I) wherein the bivalent radical of formula A represents a radical of formula (b-1) wherein $R^6$ is other than hydrogen or the bivalent radical of formula A represents a radical of formula (b-2). wherein the nitrogen atom in the is oxidized to the N-oxide.

Interesting compounds are those compounds of formula (I) wherein one or more of the following restrictions apply:
a) the bivalent radical —$Z^1$—$Z^2$— is a radical of formula (e-4);
b) $R^1$, $R^2$ and $R^3$ are each independently selected from hydrogen, $C_{1-6}$alkyl, hydroxy or halo;
c) $R^4$ is hydrogen; and/or
d) $Alk^1$ is $C_{1-2}$alkanediyl optionally substituted with hydroxy, in particular $Alk^1$ is $CH_2$.

A first group of particular compounds consists of those compounds of formula (I) wherein the bivalent radical A is of formula (b-1).

A second group of particular compounds consists of those compounds of formula (I) wherein the bivalent radical A is of formula (b-2).

Preferred compounds are those compounds of formula (I) wherein $R^5$ is a radical of formula (c-1) wherein X is oxygen, and Q is a radical of formula (d-1) or (d-2) wherein optionally one or two hydrogen atoms on the same or a different carbon atom may be replaced by $C_{1-4}$alkyl.

More preferred compounds are those compounds of formula (I) wherein $R^4$ is hydrogen: A is a radical of formula (b-1) wherein $R^6$ is hydrogen or $C_{1-6}$alkyl, and $Alk^2$ is $C_{2-4}$alkanediyl; and $R^5$ is a radical of formula (c-1) wherein X is oxygen, $R^7$ is hydrogen, and Q is (d-2).

Other more preferred compounds are those compounds of formula (I) wherein $R^4$ is hydrogen, A is a radical of formula (b-2), and $R^5$ is a radical of formula (c-1) wherein X is oxygen, $R^7$ is hydrogen, and Q is (d-2).

Most preferred compounds are
1-[3-[[(3,4-dihydro-2H-1-benzopyran-2-yl)methyl] amino]-propyl]-tetrahydro-2(1H)-pyrimidinone; a stereoisomeric form thereof or a pharmaceutically acceptable acid addition salt;
(R)-1-[3-[[(3,4-dihydro-2H-1-benzopyran-2-yl)methyl] amino]propyl]-tetrahydro-2(1H)-pyrimidinone; or a pharmaceutically acceptable acid addition salt thereof; and
(R)-1-[3-[[(3,4-dihydro-2H-1-benzopyran-2-yl)methyl] amino]propyl]tetrahydro-2(1H)-pyrimidinone [R-(R*, R*)]-2,3-dihydroxybutanedioate.

The compounds of the present invention can generally be prepared by alkylating an intermediate of formula (III) with an intermediate of formula (II), wherein W is an appropriate leaving group such is, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile or tetrahydrofuran, and optionally in the presence of a suitable base such as, for example, sodium carbonate, potassium carbonate, calciumoxide or triethylamine. Stirring may enhance the rate of the reaction. The reaction may conveniently be carried out at a temperature ranging between room temperature and the reflux temperature of the reaction mixture and, if desired, the reaction may be carried out in an autoclave at an increased pressure.

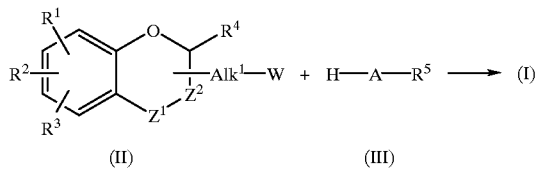

Compounds of formula (I) can also be prepared by reductively alkylating an intermediate of formula (IV), wherein Alk$^{1'}$ represents a direct bond or $C_{1-5}$alkanediyl, following art-known reductive alkylation procedures with an intermediate of formula (III).

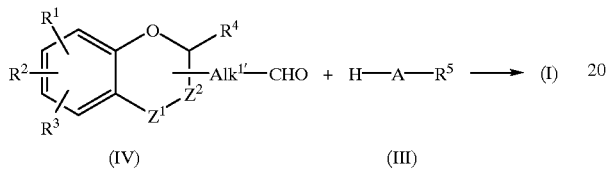

Said reductive alkylation can be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal, rhodium-on-carbon or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g. thiophene or quinoline-sulphur. To enhance the rate of the reaction, the temperature may he elevated in a range between room temperature and the reflux temperature of the reaction mixture and optionally the pressure of the hydrogen gas may be raised.

Alternatively, compounds of formula (I) can also be prepared by reacting an acid chloride of formula (V), wherein Alk$^{1'}$ represents $C_{1-5}$alkanediyl or a direct bond, with an intermediate of formula (III) under suitable reaction conditions.

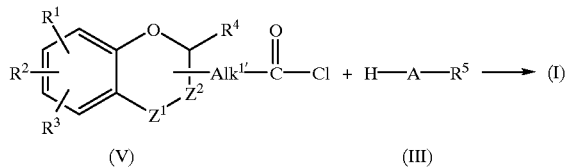

Said reaction can be performed under hydrogenation conditions with hydrogen gas in the presence of a suitable catalyst such as, for example, palladium-on-charcoal, rhodium-on-carbon or platinum-on-charcoal, in a suitable solvent such as, for example, ethyl acetate, and in the presence of magnesiumoxide. In order to prevent the undesired further hydrogenation of certain functional groups in the reactants and the reaction products, it may also be advantageous to add an appropriate catalyst-poison to the reaction mixture, e.g. thiophene or quinoline-sulphur. To enhance the rate of the reaction, the temperature may be elevated in a range between room temperature and the reflux temperature of the reaction mixture and optionally the pressure of the hydrogen gas may be raised.

Compounds of formula (I-a), defined as compounds of formula (I) wherein R$^5$ is a radical of formula (c-1) wherein R$^7$ is hydrogen, X$^1$ represents oxygen or sulfur and Q is a bivalent radical of formula (d-2), can be prepared by reacting an intermediate of formula (VI) with an intermediate of formula (VII) in a reaction-inert solvent such as, e.g. tetrahydrofuran and the like.

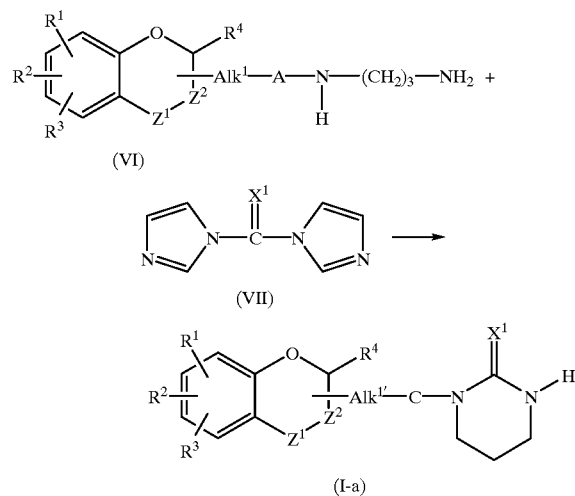

The compounds of formula (I) may further be prepared by converting compounds of formula (I) into each other according to art-known group transformation reactions. For instance, compounds of formula (I) wherein R$^6$ is phenylmethyl can be converted to the corresponding compounds of formula (I) wherein R$^6$ is hydrogen by art-known debenzylation procedures. Said debenzylation can be performed following art-known procedures such as catalytic hydrogenation using appropriate catalysts, e.g. platinum on charcoal, palladium on charcoal, in appropriate solvents such as methanol, ethanol, 2-propanol, diethyl ether, tetrahydrofuran, and the like. Furthermore, compounds of formula (I) wherein R$^6$ is hydrogen may be alkylated using art-known procedures such as, e.g. reductive N-alkylation with a suitable aldehyde or ketone, or compounds of formula (I) wherein R$^6$ is hydrogen can be reacted with an acyl halide or an acid anhydride.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g.

2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For example, a number of intermediates of formula (II), (VI) or (V) may be prepared according to art-known methodologies described in WO-93/17017 and WO-95/053837.

Compounds of formula (I) and some of the intermediates may have one or more stereogenic centers in their structure, present in a R or a S configuration, such as, e.g. the carbon atom bearing the $R^4$ substituent, and the carbon atom linked to the —$Alk^1$—A—$R^5$ moiety.

The compounds of formula (I) as prepared in the hereinabove described processes may be synthesized in the form of racemic mixtures of enantiomers which can be separated from one another following, art-known resolution procedures. The racemic compounds of formula (I) may be converted into the corresponding diastereomeric salt forms by reaction with a suitable chiral acid. Said diastereomeric salt forms are subsequently separated, for example, by selective or tractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable salts and stereoisomeric forms thereof possess favourable fundic relaxation properties as evidenced in pharmacological example C-1, the "Gastric tone measured by an electronic barostat in conscious dogs"-test.

Furthermore, as demonstrated in pharmacological example C.2 "Vasoconstrictive activity on basilar artery", the compounds of the present invention have additional beneficial pharmacological properties in that they have little or no vasoconstrictor activity. Vasoconstrictor activity can cause undesirable side-effects such as coronary spasms which can induce chest pain.

In view of the capability of the compounds of the present invention to relax the fundus, the subject compounds are useful to treat conditions related to a hampered or impaired relaxation of the fundus such as, e.g. dyspepsia, early satiety, bloating and anorexia.

Dyspepsia is described as a motility disorder. Symptoms can be caused by a delayed gastric emptying or by impaired relaxation of the fundus to food ingestion. Warm-blooded animals, including humans, (generally called herein patients) suffering from dyspeptic symptoms as a result of delayed gastric emptying usually have a normal fundic relaxation and can be relieved of their dyspeptic symptoms by administering a prokinetic agent such as, e.g. cisapride. Patients can have dyspeptic symptoms without having a disturbed gastric emptying. Their dyspeptic symptoms may result from a hypercontracted fundus or hypersensitivity resulting in a diminished compliance and abnormalities in the adaptive fundic relaxation. A hypercontracted fundus results in a diminished compliance of the stomach. The "compliance of the stomach" can be expressed as the ratio of the volume of the stomach over the pressure exerted by the stomach wall. The compliance of the stomach relates to the gastric tone, which is the result of the tonic contraction of muscle fibers of the proximal stomach. This proximal part of the stomach, by exerting a regulated tonic contraction (gastric tone), accomplishes the reservoir function of the stomach.

Patients suffering from early satiety cannot finish a normal meal since they feel saturated before they are able to finish said normal meal. Normally when a subject starts eating, the stomach will show an adaptive relaxation, i.e. the stomach will relax to accept the food that is ingested. This adaptive relaxation is not possible when the compliance of the stomach is hampered which results in an impaired relaxation of the fundus.

In view of the utility of the compounds of formula (I), it follows that the present invention also provides a method of treating warm-blooded animals, including humans, (generally called herein patients) suffering from impaired relaxation of the fundus to food ingestion. Consequently a method of treatment is provided for relieving patients suffering from conditions, such as, for example, dyspepsia, early satiety, bloating and anorexia.

Hence, the use of a compound of formula (I) as medicine is provided, and in particular the use of a compound of formula (I) for the manufacture of a medicine for treating conditions involving an impaired relaxation of the fundus to food ingestion. Both prophylactic and therapeutic treatment are envisaged.

The symptoms of impaired fundic relaxation may also arise due to the intake of chemical substances, e.g. Selective Seretonine Re-uptake Inhibitors (SSRI's), such as fluoxetine, paroxetine, fluvoxamine, citalopram and sertraline.

Another functional gastrointestinal disorder is irritable bowel syndrome whereby one of its features is believed to be related to hypersensitivity of the gut to distension. Hence it is therefore believed that modulation of said hypersensitivity by the compounds of the present invention having fundus relaxation properties may result in a reduction of the symptoms in subjects suffering from IBS. Accordingly the use of a compound of formula (I) for the manufacture of a medicine for treating IBS (irritable bowel syndrome) is provided.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g. as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica), disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

The formulations of the present invention may optionally include an anti-flatulent, such as simethicone, alpha-D-galactosidase and the like.

In general it is contemplated that a therapeutically effective amount would be from about 0.001 mg/kg to about 2 mg/kg body weight, preferably from about 0.02 mg/kg to about 0.5 mg/kg body weight. A method of treatment may also include administering the active ingredient on a regimen of between two or four intakes per day.

Experimental Part

In the procedures described hereinafter the following abbreviations were used: "ACN" stands for acetonitrile: "THF", which stands for tetrahydrofluran; "DCM" stands for dichloromethane "DIPE" stands for diisopropylether, and "DMF" means N,N-dimethyl-formamide.

For some chemicals the chemical formula was used, e.g. $H_2$ for hydrogen gas, $N_2$ for nitrogen gas, $CH_2Cl_2$ for dichloromethane, $CH_3OH$ for methanol, $NH_3$ for ammonia, HCl for hydrochloric acid, and NaOH for sodium hydroxide.

A. PREPARATION OF THE INTERMEDIATES

Example A.1 a) A solution of (+)-(R)-α-methylbelnzylamine (0.37 mol) in ethanol (100 ml) was added to a solution of 3,4-dihydro-2H-1-benzopyran-2-carboxylic acid (0.36 mol) in ethanol (200 ml). The mixture was allowed to crystallize out. The precipitate was filtered off and dried. The residue was crystallized 4 times from ethanol. The precipitate was filtered off and dried. The residue was taken up in water, treated with HCl 10% and extracted with diethyl ether. The organic layer was separated, dried, filtered and the solvent was evaporated, yielding 8.6 g of (−)-(R)-3,4-dihydro-2H-1-benzopyran-2-carboxylic acid (mp. 85.5° C., $[\alpha]_D^{20}$=−6.7° (c=100 mg/10 ml in methanol)) (interm. 1).

b) Intermediate (1) (2.14 mol) was stirred in toluene (1280 ml) under an inert atmosphere. Ethanol (640 ml) and sulfuric acid (21 ml, 96%) were added at room temperature. The reaction mixture was stirred and refluxed for 3.5 hours under an inert atmosphere. The reaction mixture was cooled to room temperature. A solution of NaHCO$_3$ (68 g) in water (1900 ml) was added slowly and this mixture was stirred for 15 minutes. The organic layer was separated, dried, filtered and the filtrate was concentrated to a 600-ml volume. The concentrate, ethyl (−)-(R)-3,4-dihydro-2H-1-benzopyran-2-carboxylic ester, was used as such in next reaction step (interm. 2).

c) A mixture of toluene (1000 ml) and ethanol (absolute, 520 ml) was stirred. Sodium borohydride (2.13 mol) was added at room temperature, under an inert atmosphere. The mixture was heated to 50° C. Intermediate (2) (2.14 mol) was added dropwise at 50° C. in a 90-minutes period (exothermic temperature rise of 15° C., cooling required). The reaction mixture was stirred for 90 minutes at 50° C. Water (1500 ml) was added while stirring. Then, 2-propanone (100 ml) was added dropwise under slight cooling. The mixture was decomposed with HCl (180 ml). The organic layer was separated, dried, filtered and the solvent evaporated, yielding 295 g of (−)-(R)-3,4-dihydro-2H-1-benzopyran-2-methanol (interm. 3).

d) A mixture of intermediate (3) (0.18 mol) in toluene (110 ml) and N,N-diethyl-ethanamine (29 ml) was stirred and cooled on an ice-bath. Methylsulfonyl chloride (0.20 mol) was added dropwise and the reaction mixture was stirred for 30 minutes at room temperature. Water was added. The organic layer was separated, washed with water, dried, filtered and the solvent was evaporated. The residue was crystallized from DIPE. The precipitate was filtered off and dried (vacuum), yielding 31.4 g (72.0%) of (R)-3,4-dihydro-2H-1-benzopyran-2-methanol methanesulfonate (ester) (interm. 4).

Example A.2 a) A mixture of (±)-3,4-dihydro-2H-benzopyran-2-carbonylchloride (0.5 mol) in N,N-dimethylacetamide (150 ml) and DIPE (350 ml) was hydrogenated with palladium on activated carbon (10%. 5.0 g) as a catalyst in the presence of a solution of thiophene in methanol (4% 4 ml). After uptake of H$_2$ (1 equivalent), the catalyst was filtered off. Potassium acetate (5 g) was added to the filtrate. Methanol (100 ml) was added, to give mixture (A). A mixture of [1-(phenylmethyl)-4-piperidinyl]-carbamic acid 1,1-dimethylethyl ester (0.45 mol) in methanol (500 ml) was hydrogenated with palladium on activated carbon (10%, 5 g) as a catalyst. After uptake of hydrogen (1 eq.), the catalyst was filtered off and the filtrate was evaporated, to give residue (B). A mixture of residue (B) in mixture (A) and methanol (100 ml) was hydrogenated with palladium on activated carbon (5 g) as a catalyst in the presence of a solution of thiophene in methanol (4%, 3 ml). After uptake of hydrogen (1 eq.), the catalyst was filtered off and the filtrate was evaporated. The residue was taken up into water, and extracted with diethyl ether. The separated organic layer was dried, filtered and the filtrate was treated with activated charcoal, then filtered over dicalite, and the solvent was evaporated. The residue was crystallized from DIPE, filtered off and dried, yielding 64.4 g (41.8%) of product (fraction 1). Part (6.3 g) of this fraction was recrystallized from DIPE, filtered off and dried, yielding 4.53 g of product. The filtrate was concentrated, stirred, and the resulting precipitate was filtered off and dried, yielding 35 g (22.4%) of (±)-1,1-dimethylethyl [1-[(3,4-dihydro-2H-1-benzopyran-2-yl) methyl]-4-piperidinyl]carbamate (fraction 2) (interm. 5).

b) A mixture of intermediate (5) (fractions 1+2) in methanol (1300 ml) and a solution of hydrochloric acid in 2-propanol (400 ml) was stirred overnight at room temperature. The precipitate was filtered off and dried, yielding 72.4 g of product. Part of this fraction was dissolved in water, alkalized, and extracted with diethyl ether. The separated organic layer was dried, filtered and the solvent evaporated, yielding 36.9 g of (±)-1-[(3,4-dihydro-2H-1-henzopyran-2-yl)methyl]-4-piperidinamine (interm. 6).

c) A mixture of intermediate (6) (0.047 mol) and acrylonitrile (0.047 mol) in ethanol (250 ml) was stirred and refluxed overnight. The solvent was evaporated. The residue was purified over silica gel on a glass filter eluent: CH$_2$Cl$_2$/CH$_3$OH from 95/5 to 90/10). The desired fractions were collected and the solvent was evaporated. Toluene was added and azeotroped on the rotary evaporator, yielding 11.5g (81.9%) of (±)-3-[[1-[(3,4-dihydro-2H-1-henzopyran-2-yl)methyl]-4-piperidinyl]amino]propanenitrile (interm. 7).

d) A mixture of intermediate (7) (0.013 mol) in a solution of ammonia in methanol (200 ml) was hydrogenated with Raney nickel (3.0 g) as a catalyst. After uptake of hydrogen (2 eq.), the catalyst was filtered off and the filtrate was evaporated, yielding 3.6g of (±)-N-[1-[(3,4-dihydro-2H-1-benzopyran-2-yl)methyl]-4-piperidinyl]-1,3-propanediamine (interm. 8).

Example A.3 a) A mixture of 1-[2-hydroxy-3-methyl-4-(phenylmethoxy)phenyl]-ethanone (0.098 mol) and ethanedioic acid, diethyl ester (0.11 mol) in toluene (100 ml) was added dropwise to a mixture of sodium methoxide (0.22 mol) in toluene (150 ml). The reaction mixture was stirred and refluxed for 2 hours. The solvent was evaporated. The residue was added to a mixture of acetic acid (150 ml) and hydrochloric acid (50 ml). The reaction mixture was stirred and refluxed for 1 hour. The mixture was poured out onto ice. The resulting precipitate was filtered off and dried (vacuum: 70° C.), yielding 29 g (95.4%) of 8-methyl-4-oxo-7-(phenylmethoxy)-4H-1-benzopyran-2-carboxylic acid (interm. 9).

b) A mixture of intermediate (9) (0.093 mol) and methanesulfonic acid (11 g) in methanol (500 ml) was hydrogenated with palladium on activated carbon (3 g) as a catalyst.

After uptake of $H_2$ (4 eq.), the catalyst was filtered off. The filtrate was evaporated. The residue was dissolved in DCM and the organic solution was washed with water, dried, filtered and the solvent was evaporated, yielding 19.2 g of (+)-methyl 3,4-dihydro-7-hydroxy-8-methyl-2H-1-benzopyran-2-carboxylate (interm. 10).

c) Reaction under $N_2$ flow. A solution of diisobutylaluminum hydride in toluene (25%) was added dropwise to a mixture of intermediate (10) (0.077 mol) in toluene (250 ml) and THF (20 ml), stirred at −70° C. The reaction mixture was stirred for one hour at −70° C., then decomposed with methanol (35 ml). The reaction mixture was poured out into water and this mixture was acidified with hydrochloric acid. The organic layer was separated, and washed with water. The aqueous phase was extracted with DCM. The combined organic layers were dried, filtered and the solvent evaporated, yielding 13 g (87.8%) of (±)-3,4-dihydro-7-hydroxy-8-methyl-2H-1-benzopyran-2-carboxaldehyde (interm. 11).

Example A.4 a) A mixture of N-[1-(phenylmethyl)-4-piperidinyl]-1,3-propanediamine (0.035 mol) and 2,2-dioxide 1,3,2-benzodioxathiole (0.035 mol) in 1,4-dioxane (250 ml) was stirred and refluxed overnight, then stirred for 2 days at 20° C. The solvent was evaporated. The residue was crystallized from $ACN/H_2O$. The precipitate was filtered off and dried, yielding 7.65 g of tetrahydro-2-[1-(phenylmethyl)-4-piperidinyl]-2H-1,2,6-thiadiazine, 1,1-dioxide (interm. 12).

b) A mixture of intermediate (12) (0.021 mol) in methanol (150 ml) was hydrogenated with palladium on activated carbon (2.0 g) as a catalyst. After uptake of $H_2$ (1 eq.), the catalyst was filtered off and the filtrate was evaporated. The residue was crystallized from ACN. The precipitate was filtered off and dried, yielding 2.3 g (50.3%) of product. The filtrate was evaporated. Toluene was added and azeotroped on the rotary evaporator, yielding 1.4 g (30.6% of tetrahydro-2-(4-piperidinyl)-2H-1,2,6-thiadiazine, 1,1-dioxide (interm. 13).

Example A.5 a) A mixture of 1-(phenylmethyl)-4-piperidinemethanamine (0.076 mol) and acrylonitrile (0.076 mol) in ethanol (250 ml) was stirred and refluxed for 4 hours. The solvent was evaporated, yielding 20.0 g (102.4%, crude residue, used in next reaction step, without further purification) of 3-[[[1-(phenylmethyl)-4-piperidinyl]methyl]-amino]-propanenitrile (interm. 14).

b) A mixture of intermediate (14) (0.078 mol) in a solution of ammonia in methanol (400 ml) was hydrogenated with Raney nickel (3 g) as a catalyst. After uptake of hydrogen (2 eq.), the catalyst was filtered off and the filtrate was evaporated, yielding 20.2 g (99.4%, used in next reaction step, without further purification) of N-[[1-(phenyl-methyl)-4-piperidinyl]methyl]-1,3-propanediamine (interm. 15).

c) A mixture of intermediate (15) (0.027 mol) and 1,1'-carbonylbis-1H-imidazole (0.027 mol) was stirred and refluxed overnight. The solvent was evaporated. The residue was purified by column chromatography over silica gel (eluent: $CH_2Cl_2/(CH_3OH/NH_3)$ 93/7). The desired frictions were collected and the solvent was evaporated, yielding 2.9 g of product. Part of this fraction (0.5 g) was recrystallized from ACN, filtered off and dried, yielding 0.14 g of tetrahydro-1-[[1-(phenylmethyl)-4-piperidinyl]-methyl]-2 (1H)-pyrimidinone (interm. 16).

d) A mixture of intermediate (16) (0.0084 mol) in methanol (150 ml) was hydrogenated with palladium on activated carbon (1 g) as a catalyst. After uptake of $H_2$ (1 eq.), the catalyst was filtered off and the filtrate was evaporated, yielding 1.25 g (75.9%) of tetrahydro-1-(4-piperidinylmethyl)-2(1H)-pyrimidinone (interm. 17).

B. PREPARATION OF THE FINAL COMPOUNDS

Example B.1

A mixture of intermediate (4) (0.011 mol), 1-(3-aminopropyl)-tetrahydro-2(1H)pyrimidinone (0.011 mol) and calcium oxide (1 g) in THF (50 ml) was stirred overnight at 100° C. (autoclave). The reaction mixture was filtered over dicalite and the filtrate was evaporated. The residue was purified by column chromatography over silica gel (eluent: $CH_2Cl_2/(CH_3OH/NH_3)$ 95/5). The pure fractions were collected and the solvent was evaporated. The residue was dissolved in ethanol and converted into the ethanedioic acid salt (1:1). The precipitate was filtered off and dried (vacuum). yielding 2.2 g (50.8%) of (R)-1-[3-[[(3,4-dihydro-2H-1-benzopyran-2-yl)methyl]amino]propyl]-tetrahydro-2(1H)-pyrimidinone ethanedioate (1:1); $[\alpha]$=−54.56° (c=0.1% in DMF) (comp. 3).

Example B.2

A mixture of 3.4-dihydro-2H-1-benzopyran-2-carboxaldehyde (0.015 mol) and 1-(3-aminopropyl) tetrahydro-2(1H)-pyrimidinethione (0.01 mol) in methanol (150 ml) was hydrogenated for 2 days at room temperature (atmospheric pressure) with palladium on activated carbon (2 g) as a catalyst. After uptake of $H_2$ (1 eq.), the catalyst was filtered off and the filtrate was evaporated. The residue was purified by column chromatography over silica gel (eluent: $C_2Cl_2/(CH_3OH/NH_3)$ 95/5). The pure fractions were collected and the solvent was evaporated. The residue (0.3 g) was dissolved in ethanol (30 ml) and converted into the ethanedioic acid salt (1:1 ) with ethanedioic acid (0.3 g; 0.0124 mol). The precipitate was filtered off and dried (vacuum), yielding 0.3 g (7%) of (±)-1-[3-[[(3,4-dihydro-2H-1-benzopyran-2-yl)-methyl]amino]propyl]tetrahydro-2 (1H)-pyrimidinethione ethanedioate(1:1); mp. 217.6° C. (comp. 14).

Example B.3

A mixture of (−)-(R)-3,4-dihydro-2H-1-benzopyran-2-carbonyl chloride (0.2 mol) and magnesium oxide (40 g) in ethyl acetate (350 ml) was hydrogenated at 25° C. with palladium on activated carbon 10% (5 g) as a catalyst in the presence of a solution (4%) of thiophene in methanol (5 ml). After uptake of $H_2$ (1 eq.), the catalyst was filtered off and the filtrate was collected in a mixture of potassium acetate (7 g) in methanol (200 ml). A mixture of 1-(3-aminopropyl)-tetrahydro-2(1H)pyrimidinone (0.2 mol) in methanol (200 ml) was added and the mixture was hydrogenated (16 hours at 25° C.; 16 hours at 50° C.) with rhodium on activated carbon (5%, 3 g) as a catalyst in the presence of a solution (4%) of thiophene in methanol (3 ml). After uptake of hydrogen, the catalyst was filtered off and the filtrate was evaporated. The residue was stirred in water, treated with 50% NaOH, and extracted with DCM. The separated organic layer was dried, filtered and the solvent evaporated. The residue was stood overnight in 2-propanone (500 ml). The supernatant was decanted off and the residue was purified by column chromatography over silica gel (eluent: $CH_2Cl_2/(CH_3OH/NH_3)$ 95/5). The desired fractions were collected and their solvent was evaporated, yielding (R)-1-[3-[[(3,4- dihydro-2H-1-benzopyran-2-yl)-methyl]amino]propyl] tetrahydro-2(1H)-pyrimidinone (comp. 2).

Example B.4

1,1'-Carbonylbis-1H-imidazole (0.02 mol) was added to a solution of (±)-N-(3-aminopropyl)-N'-[(3,4-dihydro-2H-1-benzopyran-2-yl)methyl]-N'-(phenylmethyl)-1,3-propanediamine (0.0(2 mol) in THF (100 ml). The reaction solution was stirred for 17 hours at room temperature. The solvent was evaporated. Water was added to the residue and the mixture was extracted with toluene. The organic layer was separated, dried, filtered and the solvent evaporated. The residue was crystallized from ethyl acetate (50 ml). The precipitate was filtered off and dried, yielding 3.3 g (42%) of (±)-1-[3-[[(3,4-dihydro-2H-1-benzopyran-2-yl)methyl] (phenylmethyl)amino]propyl]-tetrahydro-2(1H)-pyrimidinone (comp. 13): mp. 94.7° C.

Example B.5

Cyanocarbonimidic acid diphenyl ester (0.01 mol) was added to a solution of (±)-N-(3-aminopropyl)-N'-[(3,4-dihydro-2H-1-benzopyran-2-y)methyl]-1,3-propanediamine (0.01 mol) in DCM (100 ml), stirred at room temperature. The reaction mixture was stirred for 17 hours at room temperature. The solvent was evaporated. The residue was purified by column chromatography over silica gel (eluent: $CH_2Cl_2/(CH_3OH/NH_3)$ 95/5). The pure fractions were collected and the solvent was evaporated. The residue was dissolved in ethanol (50 ml) and converted into the ethanedioic acid salt (1:1) with ethanedioic acid (1.27 g; 0.01 mol). The precipitate was filtered off and dried (vacuum), yielding 2.5 g (59.9%) of (±)-[1-1,3-[[(3,4-dihydro-2H-1-benzopyran-2-yl)-methyl]-amino]propyl] hexahydro-2-pyrimidinylidene]cyanamide ethanedioate (1:1) (comp. 21); mp. 177.5° C.

Example B.6

A solution of compound (13) (0.009 mol) in methanol (150 ml) was hydrogenated at 50° C. with palladium on activated carbon (2 g) as a catalyst. After uptake of $H_2$ (1 eq.), the catalyst was filtered of and the filtrate was evaporated. The residue was dissolved in ethanol (100 ml) and converted into the ethanedioic acid salt (1:1) with ethanedioic acid (1.16 g; 0.009 mol). The precipitate was filtered off and dried vacuum, yielding 2.8 g (79.1%) of (±)-1-3-[[(3,4-dihydro-2H-1-benzopyran-2-yl)methyl] amino]-propyl]-tetrahydro-2(1H)-pyrimidinone ethanedioate(1:1) (comp. 1): mp. 226.3° C.

Example B.7

A mixture of compound (2) ((0.0125 mol) and 2-propanone (0.017 mol) in methanol (150 ml) was hydrogenated at 50° C. with palladium on activated carbon (2 g) as a catalyst in the presence of a solution (4%) of thiophene in methanol (2 ml). After uptake of $H_2$ (1 eq.), the catalyst was filtered off and the filtrate was evaporated. The residue was purified by column chromatography over silica gel (eluent: $CH_2Cl_2/CH_3OH/(CH_3OH/NH_3)$ 94/5/1). The pure fractions were collected and the solvent was evaporated. The residue was dried, yielding 2.226 g of (R)-1-[3-[[(3,4-dihydro-2H-1-benzopyran-2-yl)methyl](1-methylethyl) amino]propyl]tetrahydro-2(1H)-pyrimidinone (comp. 12).

Example B.8

A solution of (RR,SS)-3,4-dihydro-2-oxiranyl-2H-1-benzopyran (2.5 g) and 1-(4-piperidinyl)-2-imidazolidinone (2.4 g) in ethanol (70 ml) was stirred during 16 hours at reflux temperature. The reaction mixture was allowed to cool to room temperature and evaporated to dryness, yielding 3.7 g of (RR,SS)-1-[1-[2-(3,4-dihydro-2H-1-benzopyran-2-yl)-2-hydroxyethyl]-4-piperidinyl]-2-imidazolidinone (compound 20).

Example B.9

A mixture of N"-cyano-N-[1-[(3,4-dihydro-2H-1-benzopyran-2-yl)methyl]4-piperidinyl]-N'-(2,2-dimethoxyethyl)guanidine (0.0153 mol) and HCl (0.5 N, 46 ml) in THF (160 ml) was stirred and refluxed for 100 minutes. Ice-water was added. $Na_2CO_3$ was added portionwise to obtain a clear separation. The organic layer was separated, DCM was added, the whole was washed with water, dried, filtered and the solvent was evaporated. The residue was separated and purified by column chromatography over silica gel (separation first compound: eluent: $CH_2Cl_2/CH_3OH$ 95/5: separation second compound: $CH_2Cl_2/(CH_3OH/NH_3)$ 90/10). The two pure fraction groups were collected and their solvent was evaporated. Each residue was crystallized from ACN. Each precipitate was filtered off and dried, yielding 1.75 g [1-[1-[(3,4-dihydro-2H-1-benzopyran-2-yl)methyl]-4-piperidinyl]-1H-imidazol-2-yl]cyanamide (compound 59) and 0.48 g (±)-[1-[1-[(3,4-dihydro-2H-1-benzopyran-2-yl)methyl]-4-piperidinyl]-1H-imidazol-2-yl]urea (compound 66).

Example B.10

Compound (139) (0.0039 mol), $BBr_3$ (0.03 mol. 1 M in DCM, 30 ml) and DCM (50 ml) were mixed and cooled in an ice bath. The reaction mixture was stirred for 2 hours at 20° C. The mixture was decomposed with $H_2O/NH_4OH$ (50/50; 100 ml) while cooling on an ice bath. The mixture was stirred for one hour. The organic layer was separated, dried, filtered and the solvent was evaporated. The residue was crystallized from ethanol. The precipitate was filtered off and dried, yielding 0.60 g (±)-(R* S*)-1-[1-[2-(3,4-dihydro-8-hydroxy-2H-1-benzopyran-2-yl)-2-hydroxyethyl]-4-piperidinyl]-3,4,5,6-tetrahydro-2(1H)-pyrimidinone(compound 141).

Example B.11

A mixture of compound (150) (0.0028 mol) in methanol (100 ml) was hydrogenated with Pd/C (10%, 1.0 g) as a catalyst. After uptake of hydrogen (1 equivalent), the catalyst was filtered off and the filtrate was evaporated. The residue was dissolved in methanol/DIPE and converted into the ethanedioic acid salt (1:1). The precipitate was filtered off and dried, yielding 0.56 g (46.7%) of [R(R*,R*)]-1-[3-[[2-(3,4-dihydro-2H-1-benzopyran-2-yl)-2-hydroxyethyl] amino ]propy]-3,4,5,6-tetrahdro-2(1H-pyrimidinone ethanedioate (1:1) (compound 145).

Example B.12

A mixture of compound (34) (0.0066 mol), $Pd(OAc)_2$ (0.050 g), 1,3-propanediyl-bis[diphenylphosphine] (DPPP) (0.200 g) and $NH_3$ (20 g; gas) in THF (100 ml) was stirred overnight at 150° C. under carbon monoxide at a pressure of 0.51 $10^6$ Pa (5 atm).

The reaction mixture was filtered and the filtrate was evaporated and purified by column chromatography over silica gel (eluent: $CH_2Cl_2/(CH_3OH/NH_3)$ 95/5). The pure fractions were collected and the solvent was evaporated, yielding (±)-2-[[[3-(hexahydro-2-oxo-1-pyrimidinyl)

propyl](phenylmethyl)amino]methyl]-3,4-dihydro-2H-1-benzopyran-6-carboxamide (Compound 51).

Example B.13

Triethylamine (0.01 mol) was added to compound (3) (0.0066 mol) in DCM (50 ml). Acetylchloride (0.0066 mol) was added and the reaction mixture was stirred for 24 hours at room temperature. The mixture was washed with water, then dried, filtered and the solvent was evaporated, yielding 1.91 g of ethyl (R)-[(3,4-dihydro-2H-1-benzopyran-2-yl)methyl][3-(hexahydro-2-oxo-1-pyrimidinyl)propyl]carbamate (compound 56).

The

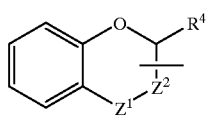

moiety in the compounds of formula (I) is numbered as follows:

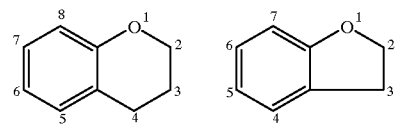

Table F-1 to F-8 list the compounds that were prepared according to one of the above Examples. The following abbreviations were used in the tables: $.C_4H_6O_5$ stands for the 2-hydroxybutanedioic acid salt (malic acid salt), $.C_2H_2O_4$ stands for the ethanedioate salt, $.C_4H_6O_6$ stands for the [R-(R*,R*)]-2,3-dihydroxy-butanedioic acid salt (L-tartaric acid salt), $.(E)-C_4H_4O_4$ stands for (E)-2-butenedioic acid salt (fumaric acid salt), $.(Z)-C_4H_4O_4$ stands for (Z)-2-butenedioic acid salt (maleic acid salt), $.C_2H_6O$ means ethanolate, $.C_3H_8O$ stands for 2-propanolate, and $c.C_6H_{11}$ stands for cyclohexyl.

TABLE F-1

| Co No. | Ex. No. | $R^1$ | $R^6$ | $R^7$ | X | Physical data |
|---|---|---|---|---|---|---|
| 1 | B.6 | H | H | H | O | $.C_2H_2O_4$ (1:1); mp. 226.3° C. |
| 2 | B.3 | H | H | H | O | (R): $[\alpha]_D^{20} = -61.19°$ (c = 0.1% in DMF) |
| 3 | B.1 | H | H | H | O | (R); $.C_2H_2O_4$ (1:1) $[\alpha]_D^{20} = -54.56°$ (c = 0.1% in DMF) |
| 4 | B.1 | H | H | H | O | (R) (+)-[R—(R*, R*)]; $.C_4H_6O_6$ (1:1).$H_2O$ (1:1) $[\alpha]_D^{20} = -45.45°$ (c = 0.1% in $CH_3OH$) |
| 5 | B.1 | H | H | H | S | (R); $.C_2H_2O_4$ (1:1); mp. 216.9° C. |
| 6 | B.1 | H | H | H | O | (S); $.C_2H_2O_4$ (1:1) $[\alpha]_D^{20} = +51.67°$ (c = 0.1% in $CH_3OH$) |
| 7 | B.3 | H | H | $c.C_6H_{11}$ | O | $.C_2H_2O_4$ (1:1) |
| 9 | B.1 | 6-F | H | H | O | $.C_2H_2O_4$ (1:1) |
| 10 | B.3 | 7-$CH_2CH_3$ | H | H | O | $.C_2H_2O_4$ (1:1); mp. 208.3° C. |
| 11 | B.1 | H | —$CH_3$ | H | O | (R) |
| 12 | B.7 | H | —$CH(CH_3)_2$ | H | O | (R) |
| 13 | B.4 | H | —$CH_2C_6H_5$ | H | O | mp. 94.7° C. |
| 14 | B.2 | H | H | H | S | (±); $.C_2H_2O_4$ (1:1); mp. 217.6° C. |
| 28 | B.3 | H | H | H | O | (R); $.(Z)-C_4H_4O_4$ (1:1) |
| 29 | B.3 | H | H | H | O | (R); $.(E)-C_4H_4O_4$ (1:1) |
| 30 | B.3 | H | H | H | O | (R), .HCl (1:1) |
| 31 | B.3 | H | H | H | O | .2HBr.$H_2O$ |
| 32 | B.3 | H | H | H | O | (R); $.C_4H_6O_5$ (1:1) .$H_2O$ (1:1) |
| 33 | B.1 | 6-Br | H | H | O | $.C_2H_2O_4$ (1:1); mp. 220.9° C. |
| 34 | B.1 | 6-Br | H | —$CH_2C_6H_5$ | O | — |
| 35 | B.1 | 6-CN | H | H | O | $.C_2H_4O_4$ (1:1); mp. 226.3° C. |
| 36 | B.1 | 7-$C(CH_3)_3$ | H | H | O | $.C_2H_2O_4$ (1:1); mp. 204.4° C. |
| 37 | B.2 | 6-$CH_3$ | H | H | O | $.C_2H_2O_4$ (1:1); mp. 215.4° C. |

TABLE F-1-continued

| Co No. | Ex. No. | R¹ | R⁶ | R⁷ | X | Physical data |
|---|---|---|---|---|---|---|
| 38 | B.2 | 6-COOC$_2$H$_5$ | H | H | O | .C$_2$H$_2$O$_4$ (1:1); mp. 226.8° C. |
| 39 | B.1 | 5-OCH$_3$ | H | H | O | .C$_2$H$_2$O$_4$ (1:1); |
| 40 | B.1 | 5-OCH$_3$ | H | H | O | — |
| 41 | B.1 | 8-OCH$_3$ | H | H | O | .C$_2$H$_2$O$_4$ (1:1); mp. 211.6° C. |
| 42 | B.1 | 8-OCH$_3$ | H | H | O | — |
| 43 | B.1 | 7-OCH$_3$ | H | H | O | .C$_2$H$_2$O$_4$ (1:1); mp. 218.3° C. |
| 44 | B.1 | 7-OCH$_3$ | H | H | O | — |
| 45 | B.1 | 6-OCH$_3$ | H | H | O | .C$_2$H$_2$O$_4$ (1:1); |
| 46 | B.1 | 6-OCH$_3$ | H | H | O | — |
| 47 | B.10 | 7-OH | H | H | O | .C$_2$H$_2$O$_4$ (2:3); mp. 165.8° C. |
| 48 | B.10 | 6-OH | H | H | O | .C$_2$H$_2$O$_4$ (2:1); .C$_2$H$_6$O (1:1) |
| 49 | B.10 | 5-OH | H | H | O | .C$_2$H$_2$O$_4$ (1:1); mp. 205.4° C. |
| 50 | B.1 | 6-NHCOCH$_3$ | H | H | O | .C$_2$H$_2$O$_4$ (1:1); mp. 215.7° C. |
| 51 | B.12 | 6-CONH$_2$ | H | —CH$_2$C$_6$H$_5$ | O | — |
| 52 | B.11 | 6-CONH$_2$ | H | H | O | .C$_2$H$_2$O$_4$ (1:1); |
| 53 | B.2 | H | H | —C$_6$H$_5$ | O | .HCl (1:1); mp. 162.5° C. |
| 54 | B.2 | H | H | —CH$_2$C$_6$H$_5$ | O | .C$_2$H$_2$O$_4$ (2:3); mp. 154.8° C. |
| 55 | B.2 | H | H | —CH(CH$_3$)$_2$ | O | .C$_2$H$_2$O$_4$ (1:1); mp. 178° C. |
| 56 | B.13 | H | H | —(CO)OCH$_2$CH$_3$ | O | (R) |
| 57 | B.13 | H | H | —(CO)OC(CH$_3$)$_3$ | O | (R) |

TABLE F-2

| Co No. | Ex. No. | R⁴ | R⁷ | =X | m | Q | Physical data |
|---|---|---|---|---|---|---|---|
| 15 | B.1 | H | H | =O | 0 | —(CH$_2$)$_2$— | mp. 144.2° C. |
| 16 | B.4 | H | H | =O | 0 | —(CH$_2$)$_3$— | — |
| 17 | B.3 | H | H | =O | 0 | —(CH$_2$)$_3$— | (R); [α]$_D^{20}$ = −73.81° (c = 0.5% in CH$_3$OH) |
| 18 | B.2 | H | H | =O | 1 | —(CH$_2$)$_3$— | (R) |
| 58 | B.8 | CH$_3$ | H | =O | 0 | —(CH$_2$)$_2$— | mp. 150.6° C. |
| 59 | B.9 | H | H | =NCN | 0 | —CH=CH— | — |
| 60 | B.2 | H | H | =O | 0 | —CH$_2$CHOHCH$_2$— | mp. 147.7° C. |
| 61 | B.2 | H | H | =O | 0 | —CH$_2$C(CH$_3$)$_2$CH$_2$— | — |

TABLE F-3
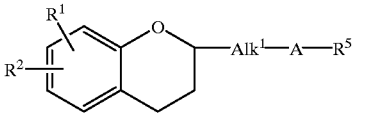
| Co No. | Ex. No. | R¹ | R² | —Alk¹—A—R⁵ | Physical data |
|---|---|---|---|---|---|
| 19 | B.2 | 7-OH | 8-CH₃ | 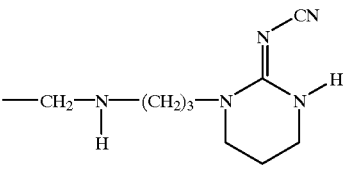 | .C₂H₂O₄ (2:1) .H₂O (1:2) |
| 21 | B.5 | H | H | 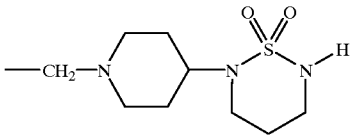 | .C₂H₂O₄ (1:1); mp. 177.5° C. |
| 22 | B.2 | H | H | 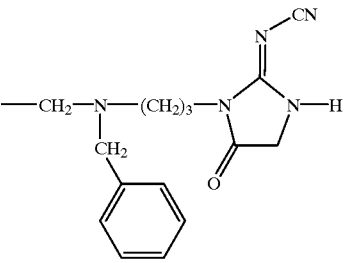 | (R) |
| 23 | B.5 | H | H | 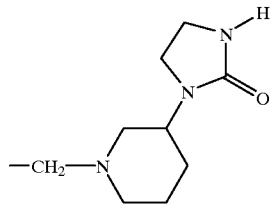 | — |
| 24 | B.2 | H | H | 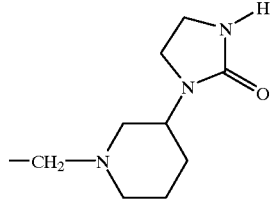 | [R, (A)] |
| 25 | B.2 | H | H | 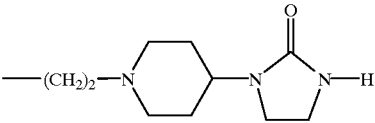 | [R, (B)] |
| 62 | B.1 | H | H | (CH₂)₂—N⟨piperidine⟩—imidazolidinone | mp. 152.5° C. |

TABLE F-3-continued

| Co No. | Ex. No. | R¹ | R² | —Alk¹—A—R⁵ | Physical data |
|---|---|---|---|---|---|
| 63 | B.1 | H | H | —(CH₂)₂—N(piperidine)—CH₂—N(imidazolidinone)—H | mp. 135.2° C. |
| 64 | B.8 | H | H | —CH(OH)—CH₂—N(piperidine)—N(imidazolidine)=N—CN | (SS, RR); mp. 202.1° C. |
| 65 | B.4 | H | H | —CH(OCH₃)—CH₂—N(piperidine)—N(imidazolidinone)—H | (±); .2H₂O.HCl |
| 66 | B.9 | H | H | —CH₂—N(piperidine)—N(imidazole)—NH—CONH₂ | — |
| 67 | B.2 | H | H | —CH₂—NH—(CH₂)₂—N(tetrahydropyrimidinone)—NH | .HCl (1:1); mp. 166.9° C. |
| 68 | B.2 | 5-CH₃ | 7-CH₃ | —CH₂—NH—(CH₂)₃—N(tetrahydropyrimidinone)—NH | .C₂H₂O₄ (1:1) |
| 69 | B.1 | H | H | —C(=O)—NH—(CH₂)₃—N(5,5-dimethyl-tetrahydropyrimidinone)—H | (R) |
| 8 | B.1 | H | H | —CH₂—NH—(CH₂)₃—N(imidazolidinone)—H | (R); .C₂H₂O₄ (1:1) [α]_D^{20} = −65.77° (c = 0.1% in DMF) |

TABLE F-3-continued

[Structure: chroman-2-yl with R¹, R² on benzene ring, substituted at 2-position with —Alk¹—A—R⁵]

| Co No. | Ex. No. | R¹ | R² | —Alk¹—A—R⁵ | Physical data |
|---|---|---|---|---|---|
| 70 | B.2 | H | H | —CH₂—NH—(CH₂)₃—[5,5-dimethyl-2-oxo-tetrahydropyrimidin-1-yl] | — |
| 71 | B.2 | H | H | —CH₂—NH—(CH₂)₃—[3-phenyl-2-oxo-imidazolidin-1-yl] | .HCl (1:1); mp. 223.9° C. |
| 72 | B.2 | H | H | —CH₂—NH—(CH₂)₃—[5-hydroxy-2-oxo-tetrahydropyrimidin-1-yl] | .C₂H₂O₄ (1:1); mp. 213.9° C. |
| 73 | B.2 | H | H | —CH₂—NH—(CH₂)₃—[2,5-dioxo-imidazolidin-1-yl] | .HCl (1:1) |

TABLE F-4

[Structure: chroman-3-yl with R¹ on benzene ring, substituted at 3-position with —Alk¹—A—R⁵]

| Co No. | Ex. No. | R¹ | —Alk¹—A—R⁵ | Physical data |
|---|---|---|---|---|
| 26 | B.1 | H | —CH₂—[4-(2-oxo-imidazolidin-1-yl)piperidin-1-yl] | mp. 181.0° C. |
| 27 | B.1 | H | —(CH₂)₂—[4-(2-oxo-imidazolidin-1-yl)piperidin-1-yl] | mp. 187.8° C. |

TABLE F-4-continued

| Co No. | Ex. No. | R[1] | —Alk[1]—A—R[5] | Physical data |
|---|---|---|---|---|
| 74 | B.4 | H | —CH₂—N(CH₂Ph)—(CH₂)₃—[tetrahydropyrimidin-2(1H)-one-1-yl] | — |
| 75 | B.6 | H | —CH₂—NH—(CH₂)₃—[tetrahydropyrimidin-2(1H)-one-1-yl] | .HCl (1:1) |
| 76 | B.2 | H | —CH₂—NH—(CH₂)₃—[5,5-dimethyltetrahydropyrimidin-2(1H)-one-1-yl] | — |
| 77 | B.2 | H | —CH₂—NH—(CH₂)₃—[1,2,6-thiadiazinane-1-yl 2,2-dioxide] | .HCl (1:1) |
| 78 | B.2 | H | —CH₂—N(piperidin-4-yl)—[tetrahydropyrimidin-2(1H)-one] | — |
| 79 | B.2 | H | —CH₂—N(piperidin-4-yl)—[imidazolidin-2-one] | $[\alpha]_D^{20} = +23.35°$, c = 4.8 mg/ml in CH₃OH |
| 80 | B.2 | H | —CH₂—N(piperidin-4-yl)—[imidazolidin-2-one] | $[\alpha]_D^{20} = -21.29°$, c = 5.1 mg/ml in CH₃OH |

TABLE F-4-continued

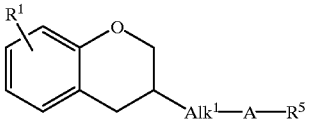

| Co No. | Ex. No. | $R^1$ | —Alk$^1$—A—R$^5$ | Physical data |
|---|---|---|---|---|
| 81 | B.2 | H | —CH$_2$—NH—(CH$_2$)$_3$—N(C(=O)N(CH$_2$-phenyl))—(CH$_2$)$_3$ ring | .C$_2$H$_2$O$_4$ (2:3); mp. 149.2° C. |
| 82 | B.2 | H | —CH$_2$—NH—(CH$_2$)$_3$—N(C(=O)N(CH$_2$-phenyl))—(CH$_2$)$_3$ ring | .C$_2$H$_2$O$_4$ (2:3) |
| 83 | B.2 | H | —CH$_2$—NH—(CH$_2$)$_3$—N(quinazoline-2,4-dione) | mp. 127.9° C. |
| 84 | B.2 | H | —CH$_2$—NH—(CH$_2$)$_3$—N(C(=O)N(CH(CH$_3$)$_2$))—(CH$_2$)$_3$ ring | .HCl (1:1); mp. 127.2° C. |
| 85 | B.2 | H | —CH$_2$—NH—(CH$_2$)$_3$—N(3,4-dihydroquinazolin-2(1H)-one) | — |
| 86 | B.2 | H | —CH$_2$—N(piperidin-4-yl with 5-hydroxy-tetrahydropyrimidin-2(1H)-one) | mp. 204.8° C. |
| 87 | B.2 | H | —CH$_2$—N(piperidin-4-yl with 5,5-dimethyl-tetrahydropyrimidin-2(1H)-one) | mp. 234.1° C. |

TABLE F-4-continued

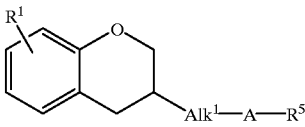

| Co No. | Ex. No. | R¹ | —Alk¹—A—R⁵ | Physical data |
|---|---|---|---|---|
| 88 | B.2 | H | —CH₂—NH—(CH₂)₃—N(tetrahydropyrimidin-2-one, 5-OH) | .C₂H₂O₄ (1:1) |
| 89 | B.2 | H | —CH₂—HN—(CH₂)₂—N(tetrahydropyrimidin-2-one) | .C₂H₄O₄ (1:1) |
| 90 | B.2 | 7-OCH₃ | —CH₂—NH—(CH₂)₃—N(tetrahydropyrimidin-2-one) | .C₂H₂O₄ (1:1) |
| 91 | B.8 | H | —CH(OH)—CH₂—N(CH₂Ph)—(CH₂)₃—N(tetrahydropyrimidin-2-one) | — |
| 92 | B.11 | H | —CH(OH)—CH₂—N(H)—(CH₂)₃—N(tetrahydropyrimidin-2-one) | .C₂H₂O₄ (1:1) |
| 93 | B.2 | 6-OCH₃ | —CH₂—NH—(CH₂)₃—N(tetrahydropyrimidin-2-one) | .C₂H₂O₄ (1:1) |
| 94 | B.2 | H | —CH₂—NH—(CH₂)₄—N(tetrahydropyrimidin-2-one) | .C₂H₂O₄ (1:1) |

TABLE F-4-continued
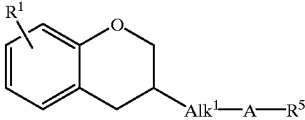
| Co No. | Ex. No. | R¹ | —Alk¹—A—R⁵ | Physical data |
|---|---|---|---|---|
| 95 | B.2 | H | 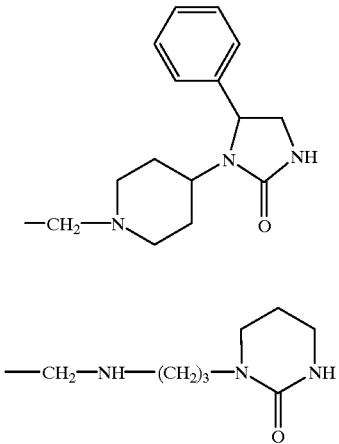 | mp. 178° C. |
| 96 | B.2 | 8-OCH₃ | 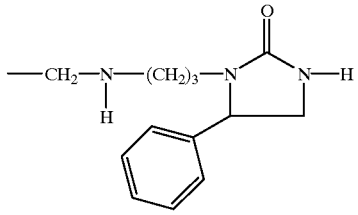 | .$C_2H_2O_4$ (1:1) |
| 97 | B.2 | H | 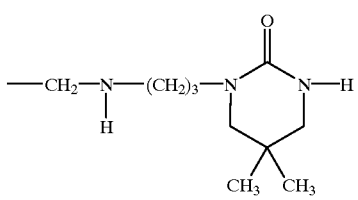 | .$C_2H_2O_4$ (1:1) |
| 98 | B.2 | 7-OCH₃ | 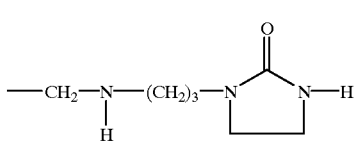 | .$C_2H_2O_4$ (1:1) |
| 99 | B.2 | H | 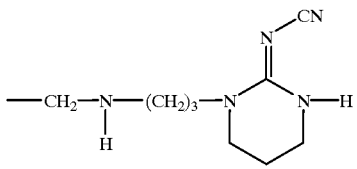 | .$C_2H_2O_4$ (1:1) |
| 100 | B.5 | H | | .$C_2H_2O_4$ (1:1) |

TABLE F-5

Structure: benzodioxane-CH2-N(piperidine)-R5

| Co. No. | Ex. No. | —R5 | Physical data |
|---|---|---|---|
| 101 | B.1 | 1-methyl-hydantoin-yl | mp. 183.5° C. |
| 102 | B.1 | 1-methyl-5,5-dimethyl-imidazolidin-2-one-yl | mp. 174–174.8° C. |
| 103 | B-1 | 1-methyl-5-ethyl-hydantoin-yl | (A); mp. 171–172° C. |
| 104 | B.1 | 1-methyl-5,5-dimethyl-hydantoin-yl | (±); mp. 160–165° C. |
| 105 | B.1 | 1,3-dimethyl-5,5-dimethyl-hydantoin-yl | .HBr (1:1); mp. 260° C. |
| 106 | B.1 | 1-methyl-2-methylthio-5-phenyl-imidazol-yl | mp. 157.3° C. |

TABLE F-6

Structure: R1-chroman-2-yl-C(R4)(OH)-CH2-A-N-C(=O)-N(R7)-Q ring

| Co No. | Ex. No. | R1 | R4 | R7 | A | Q | Physical data |
|---|---|---|---|---|---|---|---|
| 20 | B.8 | H | H | H | 1-methyl-piperidin-4-yl | —(CH2)2— | (RR, SS); mp. 178.3° C. |
| 107 | B.8 | H | H | H | 1-methyl-piperidin-4-yl | 2-methyl-pyridin-3-yl-carbonyl (*) | (SS, RR); mp. 214.4° C. |
| 108 | B.8 | H | H | H | 1-methyl-piperidin-4-yl | 2-methyl-pyridin-3-yl-carbonyl (*) | (SR, RS); mp. 194.5° C. |

TABLE F-6-continued
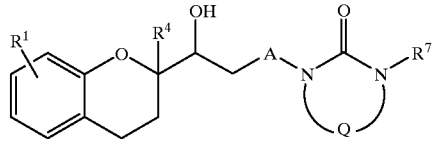
| Co No. | Ex. No. | R¹ | R⁴ | R⁷ | A | Q | Physical data |
|---|---|---|---|---|---|---|---|
| 109 | B.8 | H | H | H | 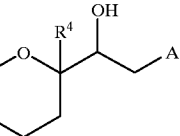 | —(CH$_2$)$_2$— | (RS, SR); mp. 193.7° C. |
| 110 | B.8 | H | H | —C$_6$H$_5$ | 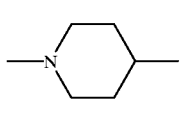 | —(CH$_2$)$_2$— | (RS, SR); mp. 172.2° C. |
| 111 | B.8 | H | H | —C$_6$H$_5$ | 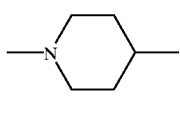 | —(CH$_2$)$_2$— | (RS, SS); mp. 192.4° C. |
| 112 | B.8 | 5-OCH$_3$ | H | H | 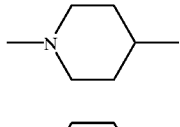 | —(CH$_2$)$_2$— | (RS, SR); mp. 203.4° C. |
| 113 | B.8 | H | CH$_3$ | H | 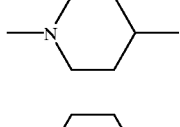 | —(CH$_2$)$_2$— | (A); mp. 175.7° C. |
| 114 | B.8 | H | H | H | 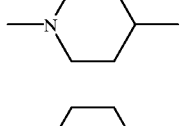 | —(CH$_2$)$_2$— | (−)-(RS); mp. 150.2° C. |
| 115 | B.8 | H | H | H | 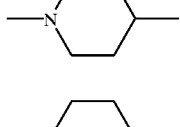 | —(CH$_2$)$_2$— | (+)-(SR); mp. 158.2° C. |
| 116 | B.8 | 6-F | H | H | 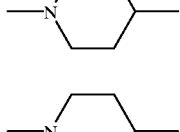 | —(CH$_2$)$_2$— | (+)-(SR); mp. 169.6° C. |
| 117 | B.8 | H | H | H | 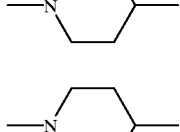 | —(CH$_2$)$_3$— | (RS, SR); mp. 186.7° C. |
| 118 | B.8 | H | H | H | 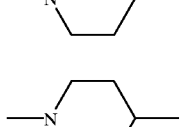 | —(CH$_2$)$_3$— | (RR, SS); mp. 195.7° C. |
| 119 | B.8 | 6-Br | H | H | 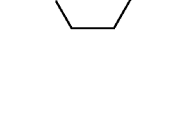 | —(CH$_2$)$_2$— | (SR, RS); mp. 180.3° C. |
| 120 | B-8 | 6-Br | H | H | 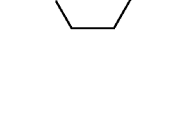 | —(CH$_2$)$_2$— | (SS, RR); mp. 183.0° C. |

TABLE F-6-continued

| Co No. | Ex. No. | $R^1$ | $R^4$ | $R^7$ | A | Q | Physical data |
|---|---|---|---|---|---|---|---|
| 121 | B.8 | 6-F | H | H | N-piperidine-4-yl (1-methyl) | —(CH$_2$)$_2$— | (−); mp. 166.1° C. |
| 122 | B.8 | 6-F | H | H | N-piperidine-4-yl (1-methyl) | —(CH$_2$)$_2$— | (+)-(SS); mp. 151.2° C. |
| 123 | B.8 | 6-F | H | H | N-piperidine-4-yl (1-methyl) | —(CH$_2$)$_2$— | (−)-(RR); mp. 160.6° C. |
| 124 | B.8 | H | H | H | N-piperidine-4-yl (1-methyl) | —CH(C$_6$H$_5$)—CH$_2$$^{(*)}$— | (RS, SR); mp. 203.4° C. |
| 125 | B.8 | H | H | H | N-piperidine-4-yl-CH$_2$— (1-methyl) | —(CH$_2$)$_2$— | (RS, SR); mp. 165.6° C. |
| 126 | B.8 | H | H | H | N-piperidine-4-yl-CH$_2$— (1-methyl) | —(CH$_2$)$_2$— | (RR, SS); mp. 168.3° C. |
| 127 | B.8 | H | H | H | N-piperidine-4-yl (1-methyl) | —(CH$_2$)$_3$— | (+)-(SR); mp. 189.6° C. |
| 128 | B.8 | H | H | H | N-piperidine-4-yl (1-methyl) | —(CH$_2$)$_3$— | (−); mp. 184.2° C. |
| 129 | B.8 | 8-OCH$_3$ | H | H | N-piperidine-4-yl (1-methyl) | —(CH$_2$)$_2$— | (RR, SS); mp. 142.6° C. |
| 130 | B.8 | 8-OCH$_3$ | H | H | N-piperidine-4-yl (1-methyl) | —(CH$_2$)$_2$— | (RS, SR); mp. 164.1° C. |
| 131 | B.8 | 8-OH | H | H | N-piperidine-4-yl (1-methyl) | —(CH$_2$)$_2$— | (RR, SS); mp. 194.6 |
| 132 | B.8 | 8-OH | H | H | N-piperidine-4-yl (1-methyl) | —(CH$_2$)$_2$— | (SR, RS); mp. 184.3° C. |

TABLE F-6-continued

| Co No. | Ex. No. | R¹ | R⁴ | R⁷ | A | Q | Physical data |
|---|---|---|---|---|---|---|---|
| 133 | B.8 | H | H | H | 1-methyl-piperidin-4-yl | C(=O)-phenyl (*) | (RR, SS); mp. 208.6° C. |
| 134 | B.8 | H | H | H | 1-methyl-piperidin-4-yl | C(=O)-phenyl (*) | (RS, SR); mp. 236.4° C. |
| 135 | B.8 | H | H | H | 1-methyl-3-methyl-piperidin-? | —(CH₂)₂— | (RS, SR); .HCl; mp. 179.9° C. |
| 136 | B.8 | H | H | H | 1-methyl-3-methyl-piperidin-? | —(CH₂)₂— | (RS, SR); .HCl; mp. 186.8° C. |
| 137 | B.8 | H | H | H | 1-methyl-piperidin-4-yl | —(CH₂)₄— | (R*, S*); mp. 164.4° C. |
| 138 | B.8 | H | H | H | 1-methyl-piperidin-4-yl | —(CH₂)₄— | (R*, R*); mp. 155.8° C. |
| 139 | B.8 | 8-OCH₃ | H | H | 1-methyl-piperidin-4-yl | —(CH₂)₃— | (R*, S*); .C₃H₈O (1:1) |
| 140 | B.8 | 8-OCH₃ | H | H | 1-methyl-piperidin-4-yl | —(CH₂)₃— | (R*, R*) |
| 141 | B.10 | 8-OH | H | H | 1-methyl-piperidin-4-yl | —(CH₂)₃— | (R*, S*) |
| 142 | B.10 | 8-OH | H | H | 1-methyl-piperidin-4-yl | —(CH₂)₃— | (R*, R*) |
| 143 | B.8 | H | H | H | —NH(CH₂)₃— | —(CH₂)₂— | (RR, SS); mp. 83.2° C. |

TABLE F-6-continued
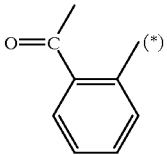
| Co No. | Ex. No. | R¹ | R⁴ | R⁷ | A | Q | Physical data |
|---|---|---|---|---|---|---|---|
| 144 | B.8 | H | H | H | —NH(CH₂)₃— | —(CH₂)₂— | (SR, RS); .C₂H₂O₄; mp. 157.9° C. |
| 145 | B.11 | H | H | H | —NH—(CH₂)₃ | —(CH₂)₃— | [R(R*, R*)]; .C₂H₂O₄ (1:1); mp. 179.7° C. |
| 146 | B.11 | H | H | H | —NH—(CH₂)₃ | —(CH₂)₃— | [S(R*, R*)]; .C₂H₂O₄ (1:1); mp. 181.8° C. |
| 147 | B.11 | H | H | H | —NH(CH₂)₃— | 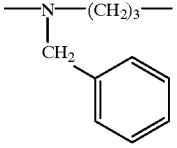 | (RR, SS); mp. 187.0° C. |
| 148 | B.8 | H | H | H | 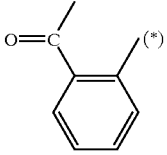 | 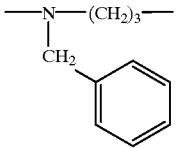 | (RS, SR); mp. 157.5° C. |
| 149 | B.8 | H | H | H | 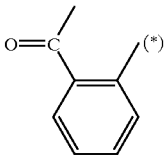 | 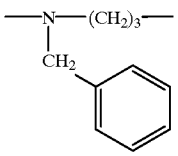 | (RR, SS) |
| 150 | B.8 | H | H | H | 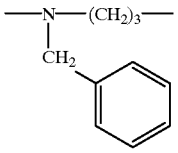 | —(CH₂)₃— | [R(R*, R*)] |
| 151 | B.8 | H | H | H | 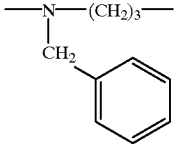 | —(CH₂)₃— | [S(R*, R*)] |
| 152 | B.8 | H | H | H | (same benzyl-N-(CH₂)₃ group) | —(CH₂)₃— | [S(R*, R*)] |

TABLE F-6-continued

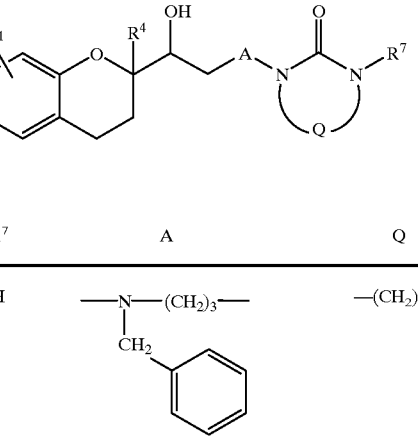

| Co No. | Ex. No. | R¹ | R⁴ | R⁷ | A | Q | Physical data |
|---|---|---|---|---|---|---|---|
| 153 | B.8 | H | H | H | —N(CH₂Ph)—(CH₂)₃— | —(CH₂)₃— | [R(R*, R*)] |
| 154 | B.11 | H | H | H | —NH(CH₂)₂— | —(CH₂)₃— | [S(R*, R*)] |
| 155 | B.11 | H | H | H | —NH(CH₂)₂— | —(CH₂)₃— | [R(R*, R*)] |

(*): attachment point to the nitrogen bearing the R⁷ group

TABLE F-7

| Co. No. | Ex. No. | Structure | Physical data |
|---|---|---|---|
| 156 | B.2 | benzofuran-2-yl-CH₂—N(4-methylpiperidinyl) | mp. 190° C. |
| 157 | B.2 | benzofuran-2-yl-CH₂—N(CH₂Ph)—(CH₂)₃— | — |
| 158 | B.11 | benzofuran-2-yl-CH₂—NH—(CH₂)₃— | .C₂H₂O₄ (1:1) |
| 159 | B.11 | 2,3-dihydrobenzofuran-2-yl-CH₂—NH—(CH₂)₃— | .C₂H₂O₄ (1:1) |

TABLE F-7-continued

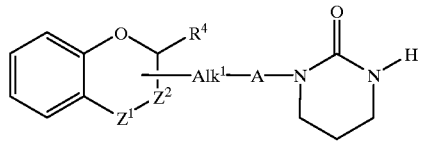

| Co. No. | Ex. No. | structure | Physical data |
|---|---|---|---|
| 160 | B.2 | (naphtho-chroman-CH₂-NH-(CH₂)₃-) | .C₂H₂O₄ (1:1); mp. 194.8° C. |
| 161 | B.2 | (chroman-4-yl-CH₂-NH-(CH₂)₃-) | .C₂H₂O₄ (1:1) |

TABLE F-8

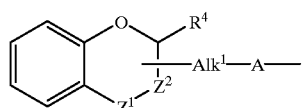

| Co. No. | Ex. No. | —$R^{1a}$—$R^{2a}$— | $Alk^2$ | Q | Physical data |
|---|---|---|---|---|---|
| 162 | B.1 | —(CH₂)₄— | —(CH₂)₃— | —(CH₂)₃— | .C₂H₂O₄ (1:1); mp. 228.8° C. |
| 163 | B.1 | —(CH₂)₄— | —(CH₂)₃— | —CH₂—C(CH₃)₃—CH₂— | .C₂H₂O₄ (1:1) |
| 164 | B.1 | —CH=CH—CH=CH— | —(CH₂)₃— | —(CH₂)₃— | .C₂H₂O₄ (1:1); mp. 228.8° C. |

C. PHARMACOLOGICAL EXAMPLES

C. 1. Gastric Tone Measured by an Electronic Barostat in Conscious Dogs

Gastric tone cannot be measured by manometric methods. Therefore an electronic barostat was used. This allows the study of the physiological pattern and regulation of gastric tone in conscious dogs and the influence of test-compounds on this tone.

The barostat consists of an air injection system which is connected by a double-lumen 14-French polyvinyl tube to an ultrathin flaccid polyethylene bag (maximal volume:±700 ml). Variations in gastric tone were measured by recording changes in the volume of air within an intragastric bag, maintained at a constant pressure, or at varying pressure levels. The barostat maintains a constant pressure (preselected) within a flaccid air-filled bag introduced into the stomach, changing the volume of air within the bag by an electronic feedback system.

Thus, the barostat measures gastric motor activity (contraction or relaxation) as changes in intragastric volume (decrease or increase resp.) at a constant intragastric pressure. The barostat consists of a strain gauge linked by an electronic relay to an air injection-aspiration system. Both the strain gauge and the injection system are connected by means of double-lumen polyvinyl tube to an ultrathin polyethylene bag. A dial in the barostat allows selection of the pressure level to be maintained within the intragastric bag.

Female beagle dogs, weighing 7–17 kg, were trained to stand quietly in Pavlov frames. They were implanted with a gastric cannula under general anaesthesia and aseptic precautions. After a median laparotomy, an incision was made through the gastric wall in longitudinal direction between the greater and the lesser curve, 2 cm above the nerves of Latarjet. The cannula was secured to the gastric wall by means of a double purse string suture and brought out via a stub wound at the left quadrant of the hypochondrium. Dogs were allowed a recovery period of two weeks.

At the beginning of the experiment, the cannula was opened in order to remove any gastric juice or food remnants. If necessary, the stomach was cleansed with 40 to 50 ml lukewarm water. The ultrathin bag of the barostat was positioned into the fundus of the stomach through the gastric cannula. In order to ensure easy unfolding of the intragastric bag during the experiment, a volume of 150–200 ml was injected into the bag by raising the pressure to maximally 14 mm Hg (about 1.87 kPa) very briefly. This procedure was repeated twice. A stabilisation period of 1 hour was allowed.

After a stabilization period of 30 minutes at an intragastric pressure of 2 mmHg (about 0.27 kPa), pressure-volume curves were constructed by increasing intragastric pressure with 2 mm Hg, (0.27 kPa ) steps (maximally 14 mm Hg (about 1.87 kPa)) (11 minutes at 2 mmHg (0.27 kPa) and 3 minutes at each pressure step). These changes in pressure could be set either manually or could be installed via a computer program (LabVIEW). At least 2 stable curves had to be observed before drug administration.

Then, the test compound was administered subcutaneously between the first 3–5 minutes at 2 mmHg (0.27 kPa). Test compounds were screened at 0.63 mg/kg s.c. Other doses and routes were tested if a test compound was shown to be active during the screening procedure. Four new pressure-volume curves were then constructed to evaluate the effect induced by the compound. Table C-1 summarizes the percentual effect on relaxation of the fundus. 1 hour after administration of the test compound.

TABLE C-1

| Co. No. | % effect | Co. No. | % effect |
|---|---|---|---|
| 1 | 23.0 | 17 | 34.9 |
| 3 | 36.2 | 20 | 9.5 |
| 6 | 7.3 | 23 | 3.6 |
| 8 | 14.0 | 24 | 16.1 |
| 9 | 16.7 | 26 | 19.4 |
| 13 | 0.4 | 27 | 21.9 |
| 15 | 12.5 | | |

C.2 VASOCONSTRICTIVE ACTIVITY ON BASILAR ARTERY

Segments of basilar arteries taken from pigs (anaesthetised with sodium pentobarbital) were mounted for recording of isometric tension in organ baths. The preparations were bathed in Krebs-Henseleit solution. The solution was kept at 37° C. and gassed with a mixture of 95% $O_2$—5% $CO_2$. The preparations were stretched until a stable basal tension of 2 grams was obtained.

The preparations were made to constrict with serotonin ($3 \times 10^{-7}$ M). The response to the addition of serotonin was measured and subsequently the serotonin was washed away. This procedure was repeated until stable responses were obtained. Subsequently the test compound was administered to the organ bath and the constriction of the preparation was measured. This constrictive response was expressed as a percentage of the response to serotonin as measured previously.

The $ED_{50}$-value (molar concentration) is defined as the concentration at which a test compound causes 50% of the constrictive response obtained with serotonin. Said $ED_{50}$-values are estimated from experiments on three different preparations. A large number of compounds were tested. The following compounds had $ED_{50}$-values higher than $1.00 \times 10^{-06}$ M: 1, 3, 6, 9, 11, 13, 14, 17, 20, 23, 26, 38, 41, 43, 45, 47, 48, 50, 52, 53, 54, 55, 59, 60, 61, 64, 65, 66, 67, 72, 73, 75, 76, 79, 80, 83, 86, 87, 88, 89, 90, 92, 93, 95, 96, 109, 114, 115, 117, 118, 119, 121, 125, 127, 128, 129, 131, 133, 137, 138, 141, 143, 147, 148, 156, 164. Compound 10 had an $ED_{50}$-value of $1.13 \times 10^{-06}$ M, and compound 21 had an $ED_{50}$-value of $5.90 \times 10^{-07}$ M.

What is claimed is:

1. A compound of formula (I)

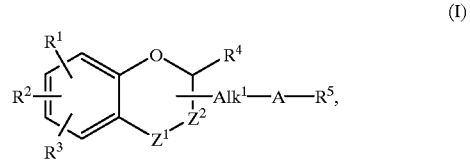

(I)

a stereochemically isomeric form thereof, an N-oxide form thereof or a pharmaceutically acceptable acid addition salt thereof, wherein $Alk^1$ is $C_{1-4}$alkylcarbonyl, $C_{1-4}$alkylcarbonyl$C_{1-4}$alkyl, carbonyl, carbonyl$C_{1-4}$alkyl, or $C_{1-6}$alkanediyl optionally substituted with hydroxy, $C_{1-4}$alkyloxy, $C_{1-4}$alkylcarbonyloxy, $C_{1-4}$alkylcarbonyloxy$C_{1-4}$ alkyloxycarbonyloxy, or $C_{3-6}$cycloalkylcarbonyloxy$C_{1-4}$alkyloxycarbonyloxy;

—$Z^1$—$Z^2$— is a bivalent radical of formula

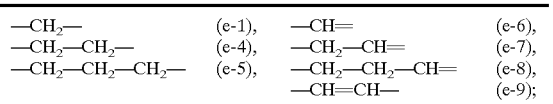

| —$CH_2$— | (e-1), | —CH= | (e-6), |
|---|---|---|---|
| —$CH_2$—$CH_2$— | (e-4), | —$CH_2$—CH= | (e-7), |
| —$CH_2$—$CH_2$—$CH_2$— | (e-5), | —$CH_2$—$CH_2$—CH= | (e-8), |
| | | —CH=CH— | (e-9); |

$R^1$, $R^2$ and $R^3$ are each independently selected from hydrogen, $C_{1-6}$alkyl, $C_{3-6}$alkenyl, $C_{1-6}$alkyloxy, trihalomethyl, trihalomethoxy, halo, hydroxy, cyano, nitro, amino, $C_{1-6}$alkylcarbonylamino, $C_{1-6}$alkyloxycarbonyl, $C_{1-4}$alkylcarbonyloxy, aminocarbonyl, mono- or di($C_{1-6}$alkyl)aminocarbonyl, amino$C_{1-6}$alkyl, mono- or di($C_{1-6}$alkyl)amino$C_{1-6}$alkyl, $C_{1-4}$alkylcarbonyloxy-$C_{1-4}$alkyloxycarbonyloxy, or $C_{3-6}$cycloalkylcarbonyloxy$C_{1-4}$alkyloxycarbonyloxy; or when $R^1$ and $R^2$ are on adjacent carbon atoms, $R^1$ and $R^2$ taken together may form a bivalent radical of formula

| —$CH_2$—$CH_2$—$CH_2$— | (a-1), |
|---|---|
| —$CH_2$—$CH_2$—$CH_2$—$CH_2$— | (a-2), |
| —$CH_2$—$CH_2$—$CH_2$—$CH_2$—$CH_2$— | (a-3), |
| —CH=CH—CH=CH— | (a-4), |
| —O—$CH_2$—O— | (a-5), |
| —O—$CH_2$—$CH_2$— | (a-6), |
| —O—$CH_2$—$CH_2$—O— | (a-7), |
| —O—$CH_2$—$CH_2$—$CH_2$— | (a-8), |
| —O—$CH_2$—$CH_2$—$CH_2$—$CH_2$— | (a-9), | wherein optionally one or two hydrogen atoms on the same or a different carbon atom may be replaced by hydroxy, $C_{1-4}$alkyl or $CH_2OH$;

$R^4$ is hydrogen, $C_{1-6}$alkyl, or a direct bond when the bivalent radical —$Z^1$—$Z^2$— is of formula (e-6), (e-7) or (e-8);

A is a bivalent radical of formula

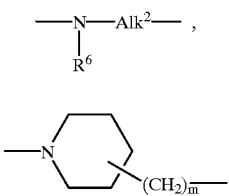   (b-1)

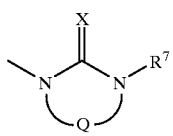   (b-2)

wherein the nitrogen atom is connected to Alk$^1$ and, m is 0 or 1;

Alk$^2$ is $C_{1-6}$alkanediyl;

$R^6$ is hydrogen, $C_{1-6}$alkyl, $C_{1-4}$alkylcarbonyl, $C_{1-4}$alkyloxycarbonyl, phenylmethyl, $C_{1-4}$alkylaminocarbonyl, $C_{1-4}$alkylcarbonyloxy-$C_{1-4}$alkyloxycarbonyl or $C_{3-6}$cycloalkylcarbonyloxy$C_{1-4}$alkyloxycarbonyloxy;

$R^5$ is a radical of formula

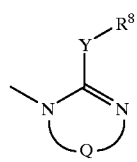   (c-1)

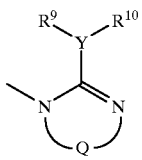   (c-2)

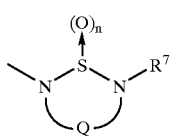   (c-3)

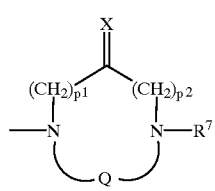   (c-4)

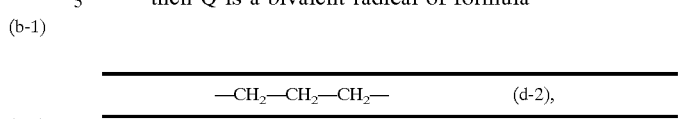   (c-5)

wherein n is 1 or 2;

X is oxygen, sulfur, $NR^9$ or $CHNO_2$;

Y is oxygen or sulfur;

$R^7$ is hydrogen, $C_{1-6}$alkyl, $C_{3-6}$cycloalkyl, phenyl or phenylmethyl;

$R^8$ is $C_{1-6}$alkyl, $C_{3-6}$cycloalkyl, phenyl or phenylmethyl;

$R^9$ is cyano, $C_{1-6}$alkyl, $C_{3-6}$cycloalkyl, $C_{1-6}$alkyloxycarbonyl or aminocarbonyl;

$R^{10}$ is hydrogen or $C_{1-6}$alkyl; and when $R^5$ is a radical of formula (c-1), (c-2), (c-3) or (c-4) then Q is a bivalent radical of formula

| —CH$_2$—CH$_2$—CH$_2$— | (d-2), |
|---|---| wherein optionally one or two hydrogen atoms on the same or a different carbon atom may be replaced by $C_{1-4}$alkyl, hydroxy or phenyl, or Q is a bivalent radical of formula

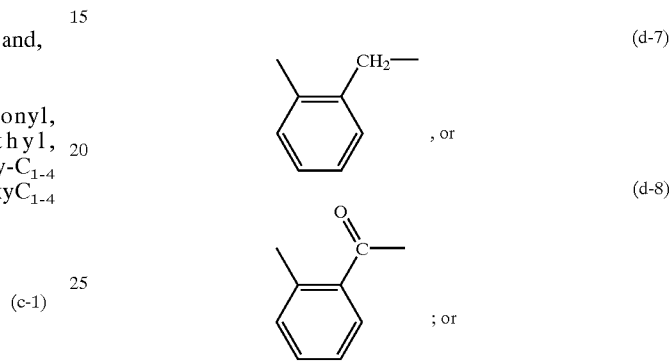

when $R^5$ is a radical of formula (c-5) then Q is a bivalent radical of formula

| —CH$_2$—CH$_2$— | (d-1), | —CH$_2$—CO— | (d-5), |
|---|---|---|---|
| —CH=CH— | (d-4), | —CO—CH$_2$— | (d-6), | wherein optionally one or two hydrogen atoms on the same or a different carbon atom may be replaced by $C_{1-4}$alkyl, hydroxy or phenyl, and $p^1$ is 0, and $p^2$ is 1; or $p^1$ is 1, and $p^2$ is 0.

2. A compound as claimed in claim 1 wherein the bivalent radical A is of formula (b-1).

3. A compound as claimed in claim 1 wherein the bivalent radical A is of formula (b-2).

4. A compound according to claim 1 wherein $R^4$ is hydrogen; A is a radical of formula (b-1) wherein $R^6$ is hydrogen or $C_{1-6}$alkyl, and Alk$^2$ is $C_{2-4}$alkanediyl; or A is a radical of formula (b-2); and $R^5$ is a radical of formula (c-1) wherein X is oxygen, $R^7$ is hydrogen, and Q is (d-2) wherein optionally one or two hydrogen atoms on the same or a different carbon atom may be replaced by $C_{1-4}$alkyl.

5. A pharmaceutical composition comprising a pharmaceutically acceptable carrier and a therapeutically active amount of a compound as claimed in claim 1.

6. A method of treating warm-blooded animals suffering from conditions related to a hampered or impaired relaxation of the fundus to food ingestion which comprises administering to said warm-blooded animal a therapeutically effective amount of a compound as defined in claim 1.

7. A method of treating warm-blooded animals suffering from dyspepsia which comprises administering to said warm-blooded animal a therapeutically effective amount of a compound as defined in claim 1.

8. A method of treating warm-blooded animals suffering from early satiety which comprises administering to said warm-blooded animal a therapeutically effective amount of a compound as defined in claim 1.

9. A method of treating warm-blooded animals suffering from bloating which comprises administering to said warm-blooded animal a therapeutically effective amount of a compound as defined in claim 1.

10. A method of treating warm-blooded animals suffering from anorexia which comprises administering to said warm-blooded animal a therapeutically effective amount of a compound as defined in claim 1.

11. A method of treating warm-blooded animals suffering from irritable bowel syndrome which comprises administering to said warm-blooded animal a therapeutically effective amount of a compound as defined in claims 1.

12. A process for preparing a compound of formula (I) wherein a) an intermediate of formula (II) is alkylated with an intermediate of formula (III) in a reaction-inert solvent and, optionally in the presence of a suitable base,

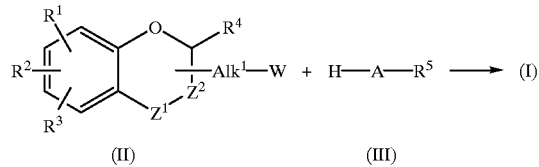

(II)                    (III)

b) an intermediate of formula (IV), wherein $Alk^{1'}$ represents a direct bond or $C_{1-5}$alkanediyl, is reductively alkylated with an intermediate of formula (III);

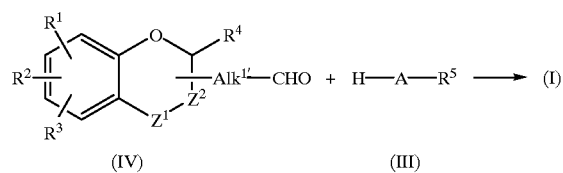

(IV)                    (III)

c) an intermediate of formula (V), wherein $Alk^{1'}$ represents a direct bond or $C_{1-5}$alkanediyl, is reacted with an intermediate of formula (III);

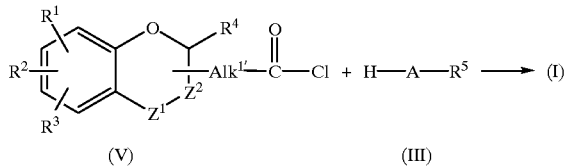

(V)                    (III)

wherein in the above reaction schemes the radicals A, $R^1$, $R^2$, $R^3$, $R^4$ and $R^5$ are as defined in claim 1 and W is an appropriate leaving group;

d) or, when $R^6$ is phenylmethyl, by reacting a compound of formula (I) with a debenzylating agent to form a compound of formula (I) wherein R6 is hydrogen; or, when $R^6$ is hydrogen, reacting a compound of formula (I) with an alkylating agent to form an N-alkyl derivative; or, when $R^6$ is hydrogen, reacting a compound of formula (I) with an acylating agent to form an N-acyl derivative; or if desired; a compound of formula (I) is converted into an acid addition salt, or conversely, an acid addition salt of a compound of formula (I) is converted into a free base form with alkali; and, if desired, preparing stereochemically isomeric forms thereof.

* * * * *